(12) United States Patent
Seidman et al.

(10) Patent No.: US 7,358,090 B2
(45) Date of Patent: Apr. 15, 2008

(54) ESTABLISHMENT OF CELLULAR MANIPULATIONS WHICH ENHANCE OLIGO-MEDIATED GENE TARGETING

(75) Inventors: Michael M. Seidman, Washington, DC (US); Alokes Majumdar, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 470 days.

(21) Appl. No.: 10/239,595

(22) PCT Filed: Mar. 22, 2001

(86) PCT No.: PCT/US01/09218

§ 371 (c)(1),
(2), (4) Date: Mar. 18, 2003

(87) PCT Pub. No.: WO01/73001

PCT Pub. Date: Oct. 4, 2001

(65) Prior Publication Data

US 2003/0211612 A1 Nov. 13, 2003

Related U.S. Application Data

(60) Provisional application No. 60/191,996, filed on Mar. 24, 2000.

(51) Int. Cl.
*C12N 15/00* (2006.01)
(52) U.S. Cl. .................... 435/440; 435/455; 536/23.1
(58) Field of Classification Search .................... None
See application file for complete search history.

(56) References Cited

U.S. PATENT DOCUMENTS 5,612,486 A * 3/1997 McConlogue .................. 800/2
6,136,601 A * 10/2000 Meyer, Jr. .................. 435/375
6,303,376 B1 * 10/2001 Glazer .................. 435/440

FOREIGN PATENT DOCUMENTS

| WO | WO 94/29461 | 12/1994 |
| WO | WO 95/01364 | 1/1995 |
| WO | WO 95/01370 | 1/1995 |
| WO | WO 95/33493 | 12/1995 |
| WO | WO 96/40271 | 12/1996 |
| WO | WO 96/40898 | 12/1996 |

OTHER PUBLICATIONS

Wening et al (Biomaterials 1995, vol. 16, pp. 337-340).*
Pilch et al. Biochemistry 1999, vol. 38, pp. 2143-2151.*
Majumdar et al. (2003, The Journal of Biological Chemistry, vol. 278, No. 13, pp. 11072-11077).*
Kurian et al (Carcinogenesis, 1992. vol. 13, No. 3, pp. 489-491).*
Majumdar et al., "Cell Cycle Modulation of Gene Targeting by a Triple Helix-forming Oligonucleotide," *The Journal of Biological Chemistry*, 278(13):11072-11077 (2003).
Puri et al., "Targeted Gene Knockout by 2'-O-Aminoethyl Modified Triplex Forming Oligonucleotides," *The Journal of Biological Chemistry*, 276(31):28991-28998 (2001).
Grisham et al., "Cycle-related toxicity and transformation in 10T1/2 cells treated with N-methyl-N'-nitro-N-nitrosoguanidine," *Proc. Natl. Acad. Sci. USA* 77(8):4813-4817, Aug. 1980.
McCormick and Bertram, "Differential cell cycle phase specificity for neoplastic transformation and mutation to ouabain residence induced by N-methyl-N'-nitro-N-nitrosoguanidine in synchronized C3H10T1/2 C18 cells," *Proc. Natl. Acad. Sci. USA* 79:4342-4346, Jul. 1982.

* cited by examiner

*Primary Examiner*—Celine Qian
(74) *Attorney, Agent, or Firm*—Klarquist Sparkman, LLP

(57) ABSTRACT

The invention relates to improved methods for the modification, including recombination, of genes in cells. More specifically, the invention relates to the increased efficiency of modification, including recombination, by introduction of a DNA-modifying molecule into a cell cycle synchronized cell. Additionally, the invention relates to target DNA that has been modified, mutated or marked by the approaches disclosed herein. The invention also relates to cells, tissue, and organisms which have been modified by the invention's methods.

16 Claims, 5 Drawing Sheets

Figure 1

|   | 5' | 3' |   | SA | Exon 5 |   |
|---|----|----|---|-----|--------|---|
|   | GA | CT |   | AG | aatgt.... | SEQ ID NO:1 |
|   |    |    |   | TC | ttaca.... | SEQ ID NO:2 |

TTTTCATTTCTCTTTTTCTTCT
AAAAGTAAAGAGAAAAAGAAGA

| TFO |  |  |
|---|---|---|
| 1 | TTTCTCTTTTCTTCT-Pso | SEQ ID NO:3 |
| 2 | TTTCGTTCTCTTTTCTTCT-Pso | SEQ ID NO:4 |
| 3 | TTTTCXTTCTCTTTTTCTTCT-Pso | SEQ ID NO:5 |
| 4 | TTTTCXTTTCTCTTTTTCTTCT-Pso | SEQ ID NO:6 |
| 5 | CXTTTCTCTTTTTCTTCT-Pso | SEQ ID NO:7 |

FIGURE 3

```
TTCATTTCTGATTTCATTTCTCTCTTTTTCTTCTAGAATGTCTTGATTGTTGAGG    SEQ ID NO:8
TTCATTTCTGATTTCATTTCTCTCTTTTTCTTCTCAAGAATGTCTTGATTGTTGAGG  SEQ ID NO:9
TTCATTTCTGATTTCATTTCTCTCTCTTTTTCTTCTGGAATGTCTTGATTGTTGAGG  SEQ ID NO:10
TTCATTTCTGATTTCATTTCTCTCTTTTTCTTTCTCATGAATGTCTTGATTGTTGAGG SEQ ID NO:11
TTCATTTCTGATTTCATTTCTCTCTTTTTCTTCTACGAATGTCTTGATTGTTGAGG   SEQ ID NO:12

TTCATTTCTGATTTCATTTCTCTCTTTTTCTTCTAGAATGTCTTGATTGTTGAGG    SEQ ID NO:13
```

Figure 4 ttcattttctgatttcatttctctcttttctttcttcagaatgtcttgattgttgagg  SEQ ID NO:13

ESTABLISHMENT OF CELLULAR MANIPULATIONS WHICH ENHANCE OLIGO-MEDIATED GENE TARGETING

CROSS REFERENCE TO RELATED APPLICATIONS

This is the U.S. National Stage of International Application No. PCT/US01/09218, filed Mar. 22, 2001, which was published under PCT Article 21(2), which in turn claims the benefit of United States Provisional Application No. 60/191,996 filed Mar. 24, 2000. All these applications are incorporated herein in their entirety.

FIELD OF THE INVENTION

This invention generally relates to novel methods to improve the efficiency of the targeting of modifications to specific locations in genomic or other nucleotide sequences. Additionally, this invention relates to target DNA that has been modified, mutated or marked by the approaches disclosed herein. The invention also relates to cells, tissue, and organisms which have been modified by the invention's methods.

BACKGROUND

The modification of genomic DNA is central to advances in biotechnology, in general, and biotechnologically based medical advances, in particular. Efficient methods for site-directed genomic modifications are desirable for research and possibly for gene therapy applications. One approach utilizes triplex-forming oligonucleotides (TFO) which bind as third strands to duplex DNA in a sequence-specific manner, to mediate directed mutagenesis. Such TFO can act either by delivering a tethered mutagen, such as psoralen or chlorambucil (Havre et al., *Proc Natl Acad Sci, U.S.A.* 90:7879-7883, 1993; Havre et al., *J Virol* 67:7323-7331, 1993; Wang et al., *Mol Cell Biol* 15:1759-1768, 1995; Takasugi et al., *Proc Natl Acad Sci, U.S.A.* 88:5602-5606, 1991; Belousov et al., *Nucleic Acids Res* 25:3440-3444, 1997), or by binding with sufficient affinity to provoke error-prone repair (Wang et al., Science 271:802-805, 1996).

Another strategy for genomic modification involves the induction of homologous recombination between an exogenous DNA fragment and the targeted gene. This approach has been used successfully to target and disrupt selected genes in mammalian cells and has enabled the production of transgenic mice carrying specific gene knockouts (Capeechi et al., *Science* 244:1288-1292, 1989; U.S. Pat. No. 4,873,191 to Wagner). This approach, however, relies on the transfer of selectable markers to allow isolation of the desired recombinants. Without selection, the ratio of homologous to nonhomologous integration of transfected DNA in typical gene transfer experiments is low, usually in the range of 1:1000 or less (Sedivy et al., *Gene Targeting*, W. H. Freeman and Co., New York, 1992). This low efficiency of homologous integration limits the utility of gene transfer for experimental use or gene therapy. The frequency of homologous recombination can be enhanced by damage to the target site from UV irradiation and selected carcinogens (Wang et al., *Mol Cell Biol* 8:196-202, 1988) as well as by site-specific endonucleases (Sedivy et al, *Gene Targeting*, W. H. Freeman and Co., New York, 1992; Rouet et al., *Proc Natl Acad Sci, U.S.A.* 91:6064-6068, 1994; Segal et al., *Proc Natl Acad Sci, U.S.A.* 92:806-810, 1995). In addition, DNA damage induced by triplex-directed psoralen photoadducts can stimulate recombination within and between extrachromosomal vectors (Segal et al., *Proc Natl Acad Sci, U.S.A.* 92:806-810, 1995; Faruqi et al., *Mol Cell Biol* 16:6820-6828, 1996; U.S. Pat. No. 5,962,426 to Glazer).

Other work has helped to define parameters that influence recombination in mammalian cells. In general, linear donor fragments are more recombinogenic than their circular counterparts (Folger et al., *Mol Cell Biol* 2:1372-1387, 1982). Recombination is also influenced by the length of uninterrupted homology between both the donor and target sites, with short fragments appearing to be ineffective substrates for recombination (Rubnitz et al., *Mol Cell Biol* 4:2253-2258, 1984). Nonetheless, several recent efforts have focused on the use of short fragments of DNA or DNA/RNA hybrids for gene correction. (Kunzelmann et al., *Gene Ther* 3:859-867, 1996).

The sequence-specific binding properties of TFO have been used to deliver a series of different molecules to target sites in DNA. For example, a diagnostic method for examining triplex interactions utilized TFO coupled to Fe-EDTA, a DNA cleaving agent (Moser et al., *Science* 238:645-650, 1987). Others have linked biologically active enzymes like micrococcal nuclease and streptococcal nuclease to TFO and demonstrated site-specific cleavage of DNA (Pei et al., *Proc Natl Acad Sci U.S.A.* 87:9858-9862, 1990; Landgraf et al., *Biochemistry* 33:10607-10615, 1994). Furthermore, site-directed DNA damage and mutagenesis can be achieved using TFO conjugated to either psoralen (Havre et al., *Proc Natl Acad Sci U.S.A.* 90:7879-7883, 1993; Takasurgi et al., *Proc Natl Acad Sci U.S.A.* 88:5602-5606, 1991) or alkylating agents (Belousov et al., *Nucleic Acids Res* 25:3440-3444, 1997; Posvic et al., *J Am Chem Soc* 112:9428-9430, 1990).

One of the major goals of biological research is the targeted modification of the genome. As noted above, although methods for delivery of genes into mammalian cells are well developed, the frequency of modification and/or homologous recombination is limited (Hanson et al., *Mol Cell Biol* 15:45-51 1995). As a result, the modification of genes is a time consuming process. Numerous methods have been contemplated or attempted to enhance modification and/or recombination between donor and genomic DNA. However, all of the present techniques suffer from low rates of modification and/or recombination or inconsistency in the modification and/or recombination rate, thereby hampering research and gene therapy technology. What is needed are methods to enhance the rates and efficiency of modifications to genomic sequences.

SUMMARY OF THE INVENTION

This invention generally relates to novel methods to improve the efficiency of the targeting of modifications to specific locations in genomic or other nucleotide sequences. Additionally, this invention relates to target DNA that has been modified, mutated or marked by the approaches disclosed herein. The invention also relates to cells, tissue, and organisms which have been modified by the invention's methods.

The present invention relates to efficient techniques and methods to enhance modification and/or recombination rates in cell lines, tissues and organisms. In particular, the invention provides a method, comprising the steps of: a) providing one or more cells wherein the cell cycle of the cells is synchronized; b) contacting the cell or cells with a means for modifying the DNA of the cells; and c) testing the cell or cells for modifications in the DNA. While not intending to limit the invention to a particular DNA modifying means, in one embodiment, the DNA modifying means comprises an oligonucleotide that is at least partly homologous to a portion of the DNA of the cells. In an alternative embodiment, contacting the cells with the DNA modifying means is at a specific point in the cell cycle, wherein the points comprise interphase, prophase, metaphase, anaphase, telophase, S phase, M phase, G0 phase, G1 phase or G2 phase. In yet another alternative embodiment, the DNA modifying means comprises a triplex forming oligonucleotide. In a further alternative embodiment, the DNA modifying means comprises a peptide nucleic acid. In yet a further embodiment, the DNA modifying means comprises a polyamide. While not intending to limit the invention to a particular type or source of cell, in one embodiment, the cells are of human origin. In another embodiment, the cells are of non-human origin. In an alternative embodiment, the cells are non-human zygotes. In yet another embodiment, at least one cell type is synchronized.

Also provided herein are cells, tissue, and organisms, that have been modified in accordance with the steps described above, i.e., a) synchronizing the cells; b) contacting the cells with a means for modifying the DNA of the cells; and c) testing the cells for modifications in the DNA.

The invention further provides a method for modifying a nucleotide sequence in the genome of a cell, comprising: a) providing: i) a cell; and ii) a DNA-modifying molecule; b) manipulating the cell to generate a synchronized cell; and c) contacting the synchronized cell with the DNA-modifying molecule under conditions such that a modification in the nucleotide sequence is produced. Without intending to limit the invention to a particular cell cycle phase, in one embodiment, the cell cycle phase of the synchronized cell is selected from the group consisting of interphase, prophase, metaphase, anaphase, telophase, S phase, M phase, G0 phase, G1 phase, and G2 phase. Without limiting the invention to a particular modification, in one embodiment, the modification is selected from the group consisting of deletion, insertion, substitution, strand break, and adduct formation. Also without limiting the invention to a particular type of DNA-modifying molecule, in one embodiment, the DNA-modifying molecule comprises an oligonucleotide of from 5 to 100 nucleotides. In another embodiment, the DNA-modifying molecule specifically binds to a nucleic acid sequence from 5 to 100 nucleotides in the genome. In yet another embodiment, the DNA-modifying molecule comprises a triplex forming oligonucleotide. In a further embodiment, the DNA-modifying molecule comprises a peptide nucleic acid. In yet a further embodiment, the DNA-modifying molecule comprises a polyamide. While it is not intended that the invention be limited to any particular type or source of cell, in one embodiment, the cell is human. In another embodiment, the cell is non-human. In an alternative embodiment, the cell is a fertilized egg cell from an animal selected from the group consisting of mouse, sheep, pig, rabbit, and cattle. In yet another embodiment, the cell is a mouse cell selected from the group consisting of blastomere cell, eight-cell embryo cell, blastocoele cell, midgestation embryo cell, and embryonic stem cell. In a further embodiment, the cell is DNA repair-deficient.

Also provided by the invention is a cell modified by a) manipulating the cell to generate a synchronized cell; and b) contacting the synchronized cell with a DNA-modifying molecule under conditions such that a modification in a nucleotide sequence in the genome of the cell is produced. Without intending to limit the invention to any particular type or source of cell, in one embodiment, the cell is human. In another embodiment, the cell is non-human. In an alternative embodiment, the cell is a fertilized egg cell from an animal selected from the group consisting of mouse, sheep, pig, rabbit, and cattle. In yet another embodiment, the cell is a mouse cell selected from the group consisting of blastomere cell, eight-cell embryo cell, blastocoele cell, midgestation embryo cell, and embryonic stem cell. In a further embodiment, the cell is DNA repair-deficient.

DESCRIPTION OF THE DRAWINGS

FIG. 1 shows sequences of Hprt target and TFOs (SEQ ID NOs:1-7) that includes the potential triplex forming site in the Chinese Hamster Hprt exon 4 and start of exon 5. The AG dinucleotides in the splice acceptor site are indicated (SA). Note that the A is preceded by a T, thereby forming a psoralen crosslink site. The A inversion in the pyrimidine run is boxed. The sequences of TFOs 1-5 are indicated. At the X position TFOs 3 and 5 have a pyrene and TFO 4 has an acridine.

FIG. 3 shows chromosomal Hprt point mutations from experiments with TFOs 3-5 (SEQ ID NOs:8-12). The triplex site is underlined and the position of the psoralen crosslink site is indicated in bold (SEQ ID NO:13). The Δ represents a base deletion. The underlined, italicized changes represent tandem events. A single example of each mutation is given, although multiple occurrences of each type were recovered in independent experiments.

FIG. 4 shows chromosomal Hprt deletions from experiments with TFOs 3-5. The triplex site is underlined and the position of the psoralen crosslink site is indicated in bold (SEQ ID NO:13). A single example of each mutation is given, although multiple occurrences of each type were recovered in independent experiments. The exact boundaries of some of the deletion mutations are ambiguous. This is reflected in the indication of the microhomology sequences, only one of which appears in the actual mutated gene.

DEFINITIONS

Figure 2:
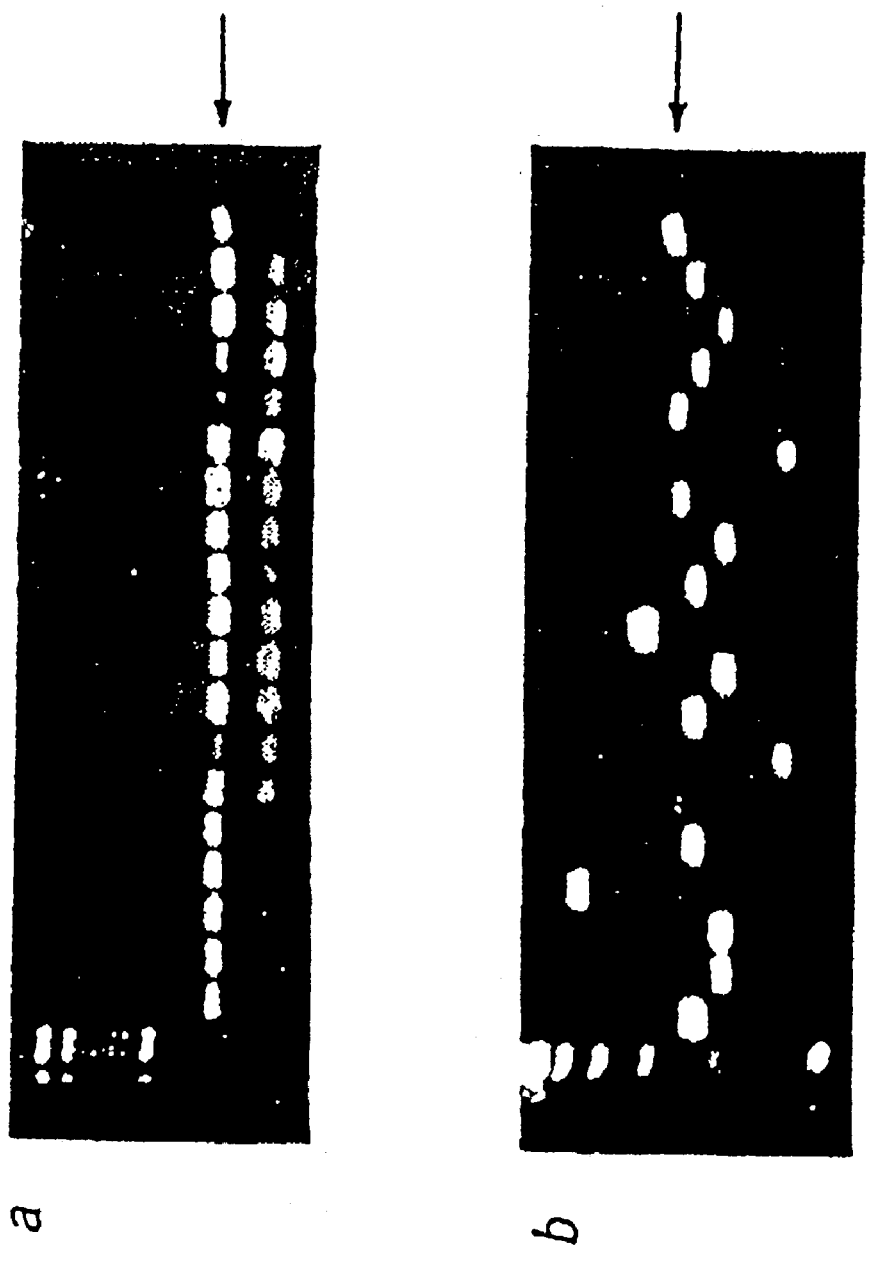
FIG. 2 shows a gel electrophoresis of exon-5 PCR products form experiments with TFOs 1, 2 (a) or 3-5 (b). The position of the wild-type fragment is indicated by the arrow.

To facilitate understanding of the invention, a number of terms are defined below.

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 100 nucleotides, preferably about 15 to 30 nucleotides, and more preferably about 20-25 nucleotides, which can be used as a probe or amplimer.

The terms "DNA-modifying molecule" and "DNA-modifying reagent" as used herein refer to a molecule which is capable of recognizing and specifically binding to a nucleic acid sequence in the genome of a cell, and which is capable of modifying a target nucleotide sequence within the genome, wherein the recognition and specific binding of the DNA-modifying molecule to the nucleic acid sequence is protein-independent. The term "protein-independent" as used herein in connection with a DNA-modifying molecule means that the DNA-modifying molecule does not require the presence and/or activity of a protein and/or enzyme for the recognition of, and/or specific binding to, a nucleic acid sequence. DNA-modifying molecules are exemplified, but not limited to triplex forming oligonucleotides, peptide nucleic acids, polyamides, and oligonucleotides which are intended to promote gene conversion. The DNA-modifying molecules of the invention are distinguished from the prior art's nucleic acid sequences which are used for homologous recombination [Wong & Capecchi (1987) Molec. Cell. Biol. 7:2294-2295] in that the prior art's nucleic acid sequences which are used for homologous recombination are protein-dependent. The term "protein-dependent" as used herein in connection with a molecule means that the molecule requires the presence and/or activity of a protein and/or enzyme for the recognition of, and/or specific binding of the molecule to, a nucleic acid sequence. Methods for determining whether a DNA-modifying molecule requires the presence and/or activity of a protein and/or enzyme for the recognition of, and/or specific binding to, a nucleic acid sequence are within the skill in the art [see, e.g., Dennis et al. (1999) Nucl. Acids Res. 27:4734-4742]. For example, the DNA-modifying molecule may be incubated in vitro with the nucleic acid sequence in the absence of any proteins and/or enzymes. The detection of specific binding between the DNA-modifying molecule and the nucleic acid sequence demonstrates that the DNA-modifying molecule is protein-independent. On the other hand, the absence of specific binding between the DNA-modifying molecule and the nucleic acid sequence demonstrates that the DNA-modifying molecule is protein-dependent and/or requires additional factors.

"Triplex forming oligonucleotide" (TFO) is defined as a sequence of DNA or RNA that is capable of binding in the major grove of a duplex DNA or RNA helix to form a triple helix. Although the TFO is not limited to any particular length, a preferred length of the TFO is 200 nucleotides or less, more preferably 100 nucleotides or less, yet more preferably from 5 to 50 nucleotides, even more perferably from 10 to 25 nucleotides, and most preferably from 15 to 25 nucleotides. Although a degree of sequence specificity between the TFO and the duplex DNA is necessary for formation of the triple helix, no particular degree of specificity is required, as long as the triple helix is capable of forming. Likewise, no specific degree of avidity or affinity between the TFO and the duplex helix is required as long as the triple helix is capable of forming. While not intending to limit the length of the nucleotide sequence to which the TFO specifically binds in one embodiment, the nucleotide sequence to which the TFO specifically binds is from 1 to 100, more preferably from 5 to 50, yet more preferably from 10 to 25, and most preferably from 15 to 25, nucleotides. Additionally, "triple helix" is defined as a double-helical nucleic acid with an oligonucleotide bound to a target sequence within the double-helical nucleic acid. The "double-helical" nucleic acid can be any double-stranded nucleic acid including double-stranded DNA, double-stranded RNA and mixed duplexes of DNA and RNA. The double-stranded nucleic acid is not limited to any particular length. However, in preferred embodiments it has a length of greater than 500 bp, more preferably greater than 1 kb and most preferably greater than about 5 kb. In many applications the double-helical nucleic acid is cellular, genomic nucleic acid. The triplex forming oligonucleotide may bind to the target sequence in a parallel or anti-parallel manner.

"Peptide Nucleic Acids," "polyamides" or "PNA" are nucleic acids wherein the phosphate backbone is replaced with an N-aminoethylglycine-based polyamide structure. PNAs have a higher affinity for complementary nucleic acids than their natural counter parts following the Watson-Crick base-pairing rules. PNAs can form highly stable triple helix structures with DNA of the following stoichiometry: $(PNA)_2$.DNA. Although the peptide nucleic acids and polyamides are not limited to any particular length, a preferred length of the peptide nucleic acids and polyamides is 200 nucleotides or less, more preferably 100 nucleotides or less, and most preferably from 5 to 50 nucleotides long. While not intending to limit the length of the nucleotide sequence to which the peptide nucleic acid and polyamide specifically binds, in one embodiment, the nucleotide sequence to which the peptide nucleic acid and polyamide specifically bind is from 1 to 100, more preferably from 5 to 50, yet more preferably from 5 to 25, and most preferably from 5 to 20, nucleotides.

The term "cell" refers to a single cell. The term "cells" refers to a population of cells. The population may be a pure population comprising one cell type. Likewise, the population may comprise more than one cell type. In the present invention, there is no limit on the number of cell types that a cell population may comprise.

The term "synchronize" or "synchronized," when referring to a sample of cells, or "synchronized cells" or "synchronized cell population" refers to a plurality of cells which have been treated to cause the population of cells to be in the same phase of the cell cycle. It is not necessary that all of the cells in the sample be synchronized. A small percentage of cells may not be synchronized with the majority of the cells in the sample. A preferred range of cells that are synchronized is between 50-100%. A more preferred range is between 75-100%. Also, it is not necessary that the cells be a pure population of a single cell type. More than one cell type may be contained in the sample. In this regard, only one of cell types may be synchronized or may be in a different phase of the cell cycle as compared to another cell type in the sample.

The term "synchronized cell" when made in reference to a single cell means that the cell has been manipulated such that it is at a cell cycle phase which is different from the cell cycle phase of the cell prior to the manipulation. Alternatively, a "synchronized cell" refers to a cell that has been manipulated to alter (i.e., increase or decrease) the duration of the cell cycle phase at which the cell was prior to the manipulation when compared to a control cell (e.g., a cell in the absence of the manipulation).

The term "cell cycle" refers to the physiological and morphological progression of changes that cells undergo when dividing (i.e. proliferating). The cell cycle is generally recognized to be composed of phases termed "interphase," "prophase," "metaphase," "anaphase," and "telophase". Additionally, parts of the cell cycle may be termed "M (mitosis)," "S (synthesis)," "G0," "G1 (gap 1)" and "G2 (gap2)". Furthermore, the cell cycle includes periods of progression that are intermediate to the above named phases.

The term "cell cycle inhibition" refers to the cessation of cell cycle progression in a cell or population of cells. Cell cycle inhibition is usually induced by exposure of the cells to an agent (chemical, proteinaceous or otherwise) that interferes with aspects of cell physiology to prevent continuation of the cell cycle.

"Proliferation" or "cell growth" refers to the ability of a parent cell to divide into two daughter cells repeatably thereby resulting in a total increase of cells in the population. The cell population may be in an organism or in a culture apparatus.

The term "capable of modifying DNA" or "DNA modifying means" refers to procedures, as well as endogenous or exogenous agents or reagents that have the ability to induce, or can aid in the induction of, changes to the nucleotide sequence of a targeted segment of DNA. Such changes may be made by the deletion, addition or substitution of one or more bases on the targeted DNA segment. It is not necessary that the DNA sequence changes confer functional changes to any gene encoded by the targeted sequence. Furthermore, it is not necessary that changes to the DNA be made to any particular portion or percentage of the cells.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequence, enhancer sequence, polyadenylation sequence, termination sequence, etc.).

"Amino acid sequence," "polypeptide sequence," "peptide sequence" and "peptide" are used interchangeably herein to refer to a sequence of amino acids.

"Target sequence," as used herein, refers to a double-helical nucleic acid comprising a sequence preferably greater than 8 nucleotides in length but less than 100 nucleotides in length. In some embodiments, the target sequence is preferably between 8 to 30 bases. The target sequence, in general, is defined by the nucleotide sequence on one of the strands on the double-helical nucleic acid.

As used herein, a "purine-rich sequence" or "polypurine sequence" when made in reference to a nucleotide sequence on one of the strands of a double-helical nucleic acid sequence is defined as a contiguous sequence of nucleotides wherein greater than 50% of the nucleotides of the target sequence contain a purine base. However, it is preferred that the purine-rich target sequence contain greater than 60% purine nucleotides, more preferably greater than 75% purine nucleotides, next most preferably greater than 90% purine nucleotides and most preferably 100% purine nucleotides.

As used herein, a "pyrimidine-rich sequence" or "polypyrimidine sequence" when made in reference to a nucleotide sequence on one of the strands of a double-helical nucleic acid sequence is defined as a contiguous sequence of nucleotides wherein greater that 50% of the nucleotides of the target sequence contain a pyrimidine base. However, it is preferred that the pyrimidine-rich target sequence contain greater than 60% pyrimidine nucleotides and more preferably greater than 75% pyrimidine nucleotides. In some embodiments, the sequence contains preferably greater than 90% pyrimidine nucleotides and, in other embodiments, is most preferably 100% pyrimidine nucleotides.

A "variant" of a first nucleotide sequence is defined as a nucleotide sequence which differs from the first nucleotide sequence (e.g., by having one or more deletions, insertions, or substitutions that may be detected using hybridization assays or using DNA sequencing). Included within this definition is the detection of alterations or modifications to the genomic sequence of the first nucleotide sequence. For example, hybridization assays may be used to detect (1) alterations in the pattern of restriction enzyme fragments capable of hybridizing to the first nucleotide sequence when comprised in a genome (i.e., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g. using fluorescent in situ hybridization (FISH) to metaphase chromosomes spreads, etc.). One example of a variant is a mutated wild type sequence.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

As used herein, the terms "mutation" and "modification" and grammatical equivalents thereof when used in reference to a nucleic acid sequence are used interchangeably to refer to a deletion, insertion, substitution, strand break, and/or introduction of an adduct. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. The term "strand break" when made in reference to a double stranded nucleic acid sequence includes a single-strand break and/or a double-strand break. A single-strand break refers to an interruption in one of the two strands of the double stranded nucleic acid sequence. This is in contrast to a double-strand break which refers to an interruption in both strands of the double stranded nucleic acid sequence. Strand breaks may be introduced into a double stranded nucleic acid sequence either directly (e.g., by ionizing radiation) or indirectly (e.g., by enzymatic incision at a nucleic acid base). Mutations may result in a mismatch. The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch is present. The terms "introduction of an adduct" or "adduct formation" refer to the covalent or non-covalent linkage of a molecule to one or more nucleotides in a DNA sequence such that the linkage results in a reduction (preferably from 10% to 100%, more preferably from 50% to 100%, and most preferably from 75% to 100%) in the level of DNA replication and/or transcription.

The terms "mutant cell" and "modified cell" refer to a cell which contains at least one modification in the cell's genomic sequence.

The term "portion" when used in reference to a nucleotide sequence refers to fragments of that nucleotide sequence.

The fragments may range in size from 5 nucleotide residues to the entire nucleotide sequence minus one nucleic acid residue.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The terms "in operable combination," "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofectin, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). When used in reference to a double-stranded nucleic acid sequence such as a cDNA or genomic clone, the term "substantially homologous" refers to any nucleic acid sequence (e.g., probe) which can hybridize to either or both strands of the double-stranded nucleic acid sequence under conditions of low stringency as described above. A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 68° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 2.0×SSPE, 0.1% SDS at room temperature when a probe of about 100 to about 1000 nucleotides in length is employed.

In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 μg/ml denatured salmon sperm DNA followed by washing in a solution comprising 0.1×SSPE and 0.1% SDS at 68° C. when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_o t$ or $R_o t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (see e.g., Anderson and Young, Quantitative Filter Hybridization, in *Nucleic Acid Hybridization* (1985)). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m°$ C. to about 20° C. to 25° C. below $T_m$. As will be understood by those of skill in the art, a stringent hybridization can be used to identify or detect identical polynucleotide sequences or to identify or detect similar or related polynucleotide sequences.

The terms "specific binding," "binding specificity," and grammatical equivalents thereof when made in reference to the binding of a first nucleotide sequence to a second nucleotide sequence, refer to the preferential interaction between the first nucleotide sequence with the second nucleotide sequence as compared to the interaction between the second nucleotide sequence with a third nucleotide sequence. Specific binding is a relative term that does not require absolute specificity of binding; in other words, the term "specific binding" does not require that the second nucleotide sequence interact with the first nucleotide sequence in the absence of an interaction between the second nucleotide sequence and the third nucleotide sequence. Rather, it is sufficient that the level of interaction between the first nucleotide sequence and the second nucleotide sequence is greater than the level of interaction between the second nucleotide sequence with the third nucleotide sequence. "Specific binding" of a first nucleotide sequence with a second nucleotide sequence also means that the interaction between the first nucleotide sequence and the second nucleotide sequence is dependent upon the presence of a particular structure on or within the first nucleotide sequence; in other words the second nucleotide sequence is recognizing and binding to a specific structure on or within the first nucleotide sequence rather than to nucleic acids or to nucleotide sequences in general. For example, if a second nucleotide sequence is specific for structure "A" that is on or within a first nucleotide sequence, the presence of a third nucleic acid sequence containing structure A will reduce the amount of the second nucleotide sequence which is bound to the first nucleotide sequence.

As used herein, the term "amplifiable nucleic acid" is used in reference to nucleic acids which may be amplified by any amplification method. It is contemplated that "amplifiable nucleic acid" will usually comprise "sample template."

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined as the production of additional copies of a nucleic acid sequence and is generally carried out using polymerase chain reaction technologies well known in the art (Dieffenbach C W and G S Dveksler (1995) *PCR Primer, a Laboratory Manual*, Cold Spring Harbor Press, Plainview, N.Y.). As used herein, the term "polymerase chain reaction" ("PCR") refers to the method of K. B. Mullis U.S. Pat. Nos. 4,683,195, and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Additionally "an oligonucleotide having a nucleotide sequence encoding a gene" may include suitable control elements such as enhancers, promoters, splice junctions, polyadenylation signals, etc. if needed to permit proper initiation of transcription and/or correct processing of the primary RNA transcript. Further still, the coding region of the present invention may contain endogenous enhancers, splice junctions, intervening sequences, polyadenylation signals, etc.

Transcriptional control signals in eukaryotes comprise "enhancer" elements. Enhancers consist of short arrays of DNA sequences that interact specifically with cellular proteins involved in transcription (Maniatis, T. et al., (1987) Science 236:1237). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, J. et al., (1989) *Molecular Cloning: A Laboratory Manual,* 2nd ed., Cold Spring Harbor Laboratory Press, New York, pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element" or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

The term "tissue specific" as it applies to a promoter refers to a promoter that is capable of directing selective expression of an oligonucleotide sequence to a specific type of tissue in the relative absence of expression of the same oligonucleotide in a different type of tissue. Tissue specificity of a promoter may be evaluated by, for example, operably linking a reporter gene to the promoter sequence to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. Selectivity need not be absolute. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of an oligonucleotide sequence in a specific type of cell in the relative absence of expression of the same oligonucleotide sequence in a different type of cell within the same tissue. The term "cell type specific" when applied to a promoter also means a promoter capable of promoting selective expression of an oligonucleotide in a region within a single tissue. Again, selectivity need not be absolute. Cell type specificity of a promoter may be assessed using methods well known in the art, e.g., immunohistochemical staining as described herein. Briefly, tissue sections are embedded in paraffin, and paraffin sections are reacted with a primary antibody which is specific for the polypeptide product encoded by the oligonucleotide sequence whose expression is controlled by the promoter. As an alternative to paraffin sectioning, samples may be cryosectioned. For example, sections may be frozen prior to and during sectioning thus avoiding potential interference by residual paraffin. A labeled (e.g., peroxidase conjugated) secondary antibody which is specific for the primary antibody is allowed to bind to the sectioned tissue and specific binding detected (e.g., with avidin/biotin) by microscopy.

The terms "selective expression," "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "contiguous" when used in reference to two or more nucleotide sequences means the nucleotide sequences are ligated in tandem either in the absence of intervening sequences, or in the presence of intervening sequences which do not comprise one or more control elements.

As used herein, the terms "nucleic acid molecule encoding," "nucleotide encoding," "DNA sequence encoding" and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "substantially purified" refers to molecules, either nucleic or amino acid sequences, that are removed from their natural environment, isolated or separated, and are at least 60% free, preferably 75% free and more preferably 90% free from other components with which they are naturally associated. An "isolated polynucleotide" is, therefore, a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "peptide transcription factor binding site" or "transcription factor binding site" refers to a nucleotide sequence which binds protein transcription factors and, thereby, controls some aspect of the expression of nucleic acid sequences. For example, Sp-1 and AP1 (activator protein 1) binding sites are examples of peptide transcription factor binding sites.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia. "Non-human animal" additionally refers to amphibians (e.g. *Xenopus*), reptiles, insects (e.g. *Drosophila*) and other non-mammalian animal species.

A "transgenic animal" as used herein refers to an animal that includes a transgene which is inserted into a cell and which becomes integrated into the genome either of somatic and/or germ line cells of the animal. A "transgene" means a DNA sequence which is partly or entirely heterologous (i.e., not present in nature) to the animal in which it is found, or which is homologous to an endogenous sequence (i.e., a sequence that is found in the animal in nature) and is inserted into the animal's genome at a location which differs from that of the naturally occurring sequence. Transgenic animals which include one or more transgenes are within the scope of this invention. Additionally, a "transgenic animal" as used herein refers to an animal that has had one or more genes modified and/or "knocked out" (made non-functional or made to function at reduced level, i.e., a "knockout" mutation) by the invention's methods, by homologous recombination, TFO mutation or by similar processes.

"Patient" is defined as a human or other animal, such as a mouse, dog, cat, horse, bovine or ovine and the like, that may be in need of alleviation or amelioration from a recognized medical condition. A "host" is defined as an animal or cell line (animal, plant or prokaryote) that can be used as a receipient for exogenous reagents and substances. In the context of the present invention, for example, a host non-human zygote may be used to generate an animal that has a gene knockout mutation, has altered expression of a protein or has increased expression of a protein. Animals with one or more of these type of mutations may have commercial value and are contemplated by the present invention.

A "transformed cell" is a cell or cell line that has acquired the ability to grow in cell culture for multiple generations, the ability to grow in soft agar, and/or the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein "exogenous" means that the gene encoding the protein is not normally expressed in the cell. Additionally, "exogenous" refers to a gene transfected into a cell to augment the normal (i.e. natural) level of expression of that gene.

A peptide sequence and nucleotide sequence may be "endogenous" or "heterologous" (i.e., "foreign"). The term "endogenous" refers to a sequence which is naturally found in the cell into which it is introduced so long as it does not contain some modification relative to the naturally-occurring sequence. The term "heterologous" refers to a sequence which is not endogenous to the cell into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes heterologous RNA and heterologous proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc.

The term "wild-type" when made in reference to a peptide sequence and nucleotide sequence refers to a peptide sequence and nucleotide sequence, respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively.

"Consensus sequence" is defined as a sequence of amino acids or nucleotides that contain identical amino acids or nucleotides or functionally equivalent amino acids or nucleotides for at least 25% of the sequence. The identical or functionally equivalent amino acids or nucleotides need not be contiguous.

General Description of the Invention

This invention generally relates to novel methods to improve the efficiency of the targeting of modifications to specific locations in genomic or other nucleotide sequences. Additionally, this invention relates to target DNA that has been modified, mutated or marked by the approaches disclosed herein. The invention also relates to cells, tissue, and organisms which have been modified by the invention's methods.

In particular, the present invention relates to the empirical discovery that the frequency of gene targeting can be substantially increased by treating the recipient cells during a specific window of time during the cell cycle (e.g., during the DNA synthesis phase of the cell cycle). This information allows investigators to increase the efficiency of the gene targeting procedure by a relatively simple manipulation of cultured cells.

The present invention generally relates to methods for the efficient modification of genomic cellular DNA and/or recombination of DNA into the genomic DNA of cells. More particularly, the present invention relates to the novel observation that the modification of genomic DNA is enhanced when the transfection of the DNA-modifying reagent is made into cell cycle-synchronized cells. In other words, cells have a higher frequency of modification of their genomic DNA if the DNA-modifying reagent is introduced into the cells during optimum points (phases) in the cell cycle. Therefore, a synchronized population of cells provides the greatest advantages in achieving the desired result of enhanced modification of genomic DNA as long as the DNA modification is performed during the optimal cell cycle period for that cell type and/or for the particular DNA-modifying reagent which is used. For example, for a given cell type, the optimum phase of the cell cycle for modifying a target DNA may be different when using DNA-modifying reagents which cause DNA strand breaks as compared to reagents which cause DNA alkylation.

Although not limited to any particular use, the methods of the present invention are useful in, for example, introducing a modification into the genome of a cell for the purpose of determining the effect of the modification on the cell. For example, A modification may be introduced into the nucleotide sequence which encodes an enzyme to determine whether the modification alters the enzymatic activity of the enzyme, and/or determine the location of the enzyme's catalytic region. Alternatively, the modification may be introduced into the coding sequence of a DNA-binding protein to determine whether the DNA binding activity of the protein is altered, and thus to delineate the particular DNA-binding region within the protein. Yet another alternative is to introduce a modification into a non-coding regulatory sequence (e.g., promoter, enhancer, etc.) in order to determine the effect of the modification on the level of expression of a second sequence which is operably linked to the non-coding regulatory sequence. This may be desirable to, for example, define the particular sequence which possesses regulatory activity.

A further alternative use for the invention's methods is the generation of transgenic cells and transgenic animals which are useful as models for diseases, and for screening therapeutic reagents. For example, where a particular modification to a gene in a first animal (e.g., human) is known or thought to be associated with a disease (e.g., lung cancer), the invention's methods may be used to introduce the same or similar modification into the genome of another animal (e.g., mouse) in order to generate a transgenic animal which may be used as a model for the disease in the first animal. Transgenic animals may be generated using several methods which are known in the art, including microinjection, retroviral infection, and implantation of embryonic stem cells. For example, modifications may be introduced into fertilized eggs, cells from pre-implantation embryos such as blastomeres, eight-cell embryos, blastocoele, and midgestation embryos, and into embryonic stem (ES) cells.

Yet another use of the invention's methods is for targeted recombination for the purpose of producing gene knockout organisms and/or of replacement of defective genes with non-defective genes. It is well established that the frequencies of existing protocols for homologous recombination in mammalian cells are quite low. However, using the invention's methods, the frequency can be dramatically increased (thousandfold) by introduction of a double strand break into the target site. Reagents that are capable of targeting double strand breaks to specific chromosomal sites may be utilized in protocols that include donor DNA and that have as an outcome efficient targeted recombination. This would be useful for the construction of transgenic animals and cell lines as described above, and also for the correction of existing gene defects at the site of the defect. For example, in one embodiment, it is contemplated that stem cells (e.g., from bone marrow, blood, etc.) are isolated from a patient or host, a defective gene is deleted or repaired, and the cells are transferred back into the patient or host to populate the bone marrow with treated stem cells. The methods of the present invention will help ensure the efficiency of the modification and/or recombination phase of the procedure, thereby increasing the likelihood of success. This approach has the advantage of a genetic in situ correction, rather than the current approach of introducing a separate copy of a gene that integrates at a site other than the natural site, and that is often subject to regulation that is different from the native gene. When homologous recombination is desired, standard techniques to select for homologous recombination of a sequence into the matching chromosomal locus may be used (Mansour et al., *Nature* 336:348-352, 1988).

TFOs are useful in targeted gene recombination. In this regard, triplex forming oligonucleotides are useful in targeting specific gene sequences (see, e.g., U.S. Pat. No. 5,962, 426, to Glazer, herein incorporated by reference). When coupled to a mutagen, TFO reagents are capable of disrupting the sequence of the targeted gene thereby effectively blocking transcription and translation of a functional product. Additionally, TFOs direct mutagenesis by binding to genomic DNA with sufficient affinity to produce error-prone repair.

Other DNA-modifying molecules may be used in targeted gene recombination. For example, peptide nucleic acids may be used to induce modifications to the genome of the target cell or cells (see, e.g., U.S. Pat. No. 5,986,053, to Ecker, herein incorporated by reference). In brief, synthetic nucleotides comprising, at least, a partial peptide backbone are used to target a homologous genomic nucleotide sequence. Upon binding to the double-helical DNA, or through a mutagen ligated to the peptide nucleic acid, modification of the target DNA sequence and/or recombination is induced to take place. Targeting specificity is determined by the degree of sequence homology between the targeting sequence and the genomic sequence.

A further application of the invention's methods is in determining the function of a gene of unknown function. This is of particular interest, given the current concern for characterizing the many new genes described by the Genome Project. For example, if a transgenic animal, which is constructed using the invention's methods that result in knockout of a gene of unknown function, were to develop cancer, it could be concluded that the function of the gene was related to the regulation of cellular growth in the tissues in which the cancer originated. Alternatively, if the animal developed muscular disorders it could be concluded that the novel gene played a role in the normal development and function of muscle tissue.

The present invention is not limited to any particular physiological mechanism. However, the following description is provided to orientate the reader to the field of targeted DNA modification. DNA in a cell is not a pure molecular species as in the test tube. Indeed, it is associated with protein to form a chromatin and chromosome complex. The association with chromosomal proteins may mask the target sequence and preclude recognition and binding by the reagent. It is well established that chromatin structure is dynamic and that there is a variability of DNA metabolic activity (transcription, replication, recombination) during the cell cycle. Thus, the accessibility of a particular target site would be expected to vary as it is engaged in these activities. Since these activities can vary as a function of the cell cycle (and must be in the case of replication) the accessibility of a particular target site may then vary as a function of the cell cycle.

It is well established that certain DNA damaging treatments are more mutagenic at certain times of the cell cycle than others. Thus, cells treated with UV light are more likely to be mutagenized at specific loci when treated in S phase (i.e., the phase in which DNA synthesis occurs) than in early G1 (i.e., the "resting" phase between mitosis and S phase). This is because replication of photoproducts may have a mutational outcome while repair of UV adducts is relatively error free. Cells treated in G1 phase have a longer time to repair than cells treated in S phase, and thus have fewer adducts when they come into S phase. Other repair functions may be more active or more important at different phases of the cell cycle. Thus, for a given DNA reactive compound increased and/or optimal efficacy may also be modulated by the cell cycle status of the treated cells. As noted previously, the optimal cell cycle time (i.e., the time at which the frequency of DNA modification is maximally increased in response to a particular treatment) may differ with different targeting reagents, different associated reagents, different cell types and different desired outcomes. In this regard, the present invention is not limited to any particular cell cycle stage, method of DNA targeting, cell type or desired effect, so long as the cell cycle of the cell or cells are synchronized and the cells are treated with the DNA modifying reagent or reagents at the optimal cell cycle phase for modification and/or recombination (if any) for that cell type.

The present invention also relates to the optimization of DNA targeting events and the process of sequence modulation stimulated by the targeting event. In this regard, the use of triple helix forming oligonucleotides (TFOs) provides a useful illustration of the efficacy of this approach. However, successful protocols are not limited to the use of TFOs. In other embodiments, the targeting reagent is exemplified, but not limited to, peptide nucleic acids (PNAs), polyamide-polypyrroles, oligonucleotides designed for marker rescue, sequence specific zinc finger proteins or reagents to induce modification and/or double-cross homologous recombination. Each of these additional embodiments are useful in provoking sequence modulation of a target as a consequence of target binding, or can be used to deliver DNA reactive reagents which then initiate the desired event pathway. Associated reagents include, but are not limited to, crosslinkers, alkylators, base modifiers, DNA breakers, free radical generators and other reagents suitable for use in the present invention. These reagents can be delivered to cells by a variety of delivery technologies, including, but not limited to, electroporation, liposomes, porphyrins, associated protein delivery reagents, passive uptake and any other suitable delivery means.

Furthermore, the present invention is not limited to the particular methods which are used herein to execute modification of genomic sequences. Indeed, a number of methods are contemplated. For example, genes may be targeted using triple helix forming oligonucleotides (TFO). TFOs may be generated synthetically, for example, by PCR or by use of a gene synthesizer apparatus. Additionally, TFOs may be isolated from genomic DNA if suitable natural sequences are found. TFOs may be used in a number of ways, including, for example, by tethering to a mutagen such as, but not limited to, psoralen or chlorambucil (see, e.g., Havre et al., *Proc Natl Acad Sci, U.S.A.* 90:7879-7883, 1993; Havre et al., *J Virol* 67:7323-7331, 1993; Wang et al., *Mol Cell Biol* 15:1759-1768, 1995; Takasugi et al., *Proc Natl Acad Sci, U.S.A.* 88:5602-5606, 1991; Belousov et al., *Nucleic Acids Res* 25:3440-3444, 1997). Furthermore, for example, TFOs may be tethered to donor duplex DNA (see, e.g., Chan et al., *J Biol Chem* 272:11541-11548, 1999). TFOs can also act by binding with sufficient affinity to provoke error-prone repair (Wang et al., *Science* 271:802-805, 1996).

While the invention's methods are illustrated using TFOs that target the DNA-modifying reagent psoralen, the invention's methods are not limited to the nature or type of DNA-modifying reagent which is used. For example, the prior art describes several DNA-modifying reagents which have been linked to oligonucleotides to form TFOs and which have been shown to be reactive with target DNA sequences in that format. For example, such DNA-modifying reagents release radicals which result in DNA strand breakage. Alternatively, the reagents alkylate DNA to form adducts which would block replication and transcription. In another alternative, the reagents generate crosslinks or molecules that inhibit cellular enzymes leading to strand breaks. Examples of DNA-modifying reagents which have been linked to oligonucleotides to form TFOs include, but are not limited to, indolocarbazoles, napthalene diimide (NDI), transplatin, bleomycin, analogues of cyclopropapyrroloindole, and phenanthodihydrodioxins. In particular, indolocarbazoles are topoisomerase I inhibitors. Inhibition of these enzymes results in strand breaks and DNA protein adduct formation [Arimondo et al., Bioorganic and Medicinal Chem. 8, 777, 2000]. NDI is a photooxidant that can oxidize guanines which could cause mutations at sites of guanine residues [Nunez, et al., Biochemistry, 39, 6190, 2000]. Transplatin has been shown to react with DNA in a triplex target when the TFO is linked to the reagent. This reaction causes the formation of DNA adducts which would be mutagenic [Columbier, et al., Nucleic Acids Research, 24, 4519, 1996]. Bleomycin is a DNA breaker, widely used as a radiation mimetic. It has been linked to oligonucleotides and shown to be active as a breaker in that format [Sergeyev, Nucleic Acids Research 23, 4400, 1995; Kane, et al., Biochemistry, 34, 16715, 1995]. Analogues of cyclopropapyrroloindole have been linked to TFOs and shown to alkylate DNA in a triplex target sequence. The alkylated DNA would then contain chemical adducts which would be mutagenic [Lukhtanov, et al., Nucleic Acids Research, 25, 5077, 1997]. Phenanthodihydrodioxins are masked quinones that release radical species upon photoactivation. They have been linked to TFOs and have been shown to introduce breaks into duplex DNA on photoactivation [Bendinskas et al., Bioconjugate Chem. 9, 555, 1998].

Other methods of inducing modifications and/or recombination are contemplated by the present invention. For example, another embodiment involves the induction of homologous recombination between an exogenous DNA fragment and the targeted gene (see e.g., Capecchi et al., Science 244:1288-1292, 1989) or by using peptide nucleic acids (PNA) with affinity for the targeted site. Still other methods include sequence specific DNA recognition and targeting by polyamides (see e.g., Dervan et al., *Curr Opin Chem Biol* 3:688-693, 1999; Biochemistry 38:2143-2151, 1999) and the use of zinc finger proteins.

The present invention is not limited to any particular frequency of modification and/or recombination. The invention's methods result in a frequency of modification in the target nucleotide sequence of from 0.2% to 3%. Nonetheless, any frequency (i.e., between 0% and 100%) of modification and/or recombination is contemplated to be within the scope of the present invention. The frequency of modification and/or recombination is dependent on the method used to induce the modification and/or recombination, the cell type used, the specific gene targeted and the DNA mutating reagent used, if any. Additionally, the method used to detect the modification and/or recombination, due to limitations in the detection method, may not detect all occurrences of modification and/or recombination. Furthermore, some modification and/or recombination events may be silent, giving no detectable indication that the modification and/or recombination has taken place. The inability to detect silent modification and/or recombination events gives an artificially low estimate of modification and/or recombination. Because of these reasons, and others, the invention is not limited to any particular modification and/or recombination frequency. In one embodiment, the frequency of modification and/or recombination is between 0.01% and 100%. In another embodiment, the frequency of modification and/or recombination is between 0.01% and 50%. In yet another embodiment, the frequency of modification and/or recombination is between 0.1% and 10%. In still yet another embodiment, the frequency of modification and/or recombination is between 0.1% and 5%.

The term "frequency of mutation" as used herein in reference to a population of cells which are treated with a DNA-modifying molecule that is capable of introducing a mutation into a target site in the cells' genome, refers to the number of cells in the treated population which contain the mutation at the target site as compared to the total number of cells which are treated with the DNA-modifying molecule. For example, with respect to a population of cells which is treated with the DNA-modifying molecule TFO tethered to psoralen which is designed to introduce a mutation at a target site in the cells' genome, a frequency of mutation of 5% means that of a total of 100 cells which are treated with TFO-psoralen, 5 cells contain a mutation at the target site.

Although the present invention is not limited to any degree of precision in the modification and/or recombination of DNA in the cell, it is contemplated that some embodiments of the present invention require higher degrees of precision, depending on the desired result. For example, the specific sequence changes required for gene repair (e.g., particular base changes) require a higher degree of precision as compared to producing a gene knockout wherein only the disruption of the gene is necessary. With the methods of the present invention, achievement of higher levels of precision in modification and/or homologous recombination techniques is greater than with prior art methods.

The present invention also contemplates the modification of DNA in cultures of synchronized cells (i.e., cells in which the cell cycle has been synchronized). The present invention is not limited to any particular method to synchronize the cell cycle. Indeed, a number of different methods are contemplated for synchronization of the cell cycle. For example, the cell cycle may be synchronized at the G2/M boundary by culture with 12-O-tetradecanoyl phorbol-13-acetate (TPA; see e.g., Arita et al., *Exp Cell Res* 242:381-390, 1998), by culture in minimal medium (see e.g., Isakson et al., *J Immunol Methods* 145:137-142, 1991), by limited cell attachment time followed by removal of unattached cells (see e.g., Held et al., *In Vitro Cell Dev Biol* 25:1025-1030, 1989), by culture with aphidicolin, or other DNA polymerase inhibitors, to induce an S phase block (see e.g., Matherly et al., *Anal Biochem* 182:338-345, 1989), by density arrest (see e.g., Takimoto et al., *FEBS Lett* 247:173-176, 1989), by double isoleucine block (see e.g., Taldmoto et al., *FEBS Lett* 247:173-176, 1989), by culture with nocodazole (see e.g., Nusse et al., *Cell Tissue Kinet* 17:13-23, 1984) or other microtubule formation inhibitor (e.g. colchicine) or by a combination of one or more of the above mentioned methods (see e.g., Cao et al., *Exp Cell Res* 193:405-410).

The present invention is also not limited to any particular method to detect cell cycle synchronization. Indeed, a number of methods are contemplated. For example, cell cycle synchronization can be determined by visual observation with light microscopy. Also, synchronization can be detected by staining with DNA intercalating reagents such as propidium iodide or acridine orange. Cell cycle stage can then be determined with flourescent microscopy of flow cytometry.

Furthermore, the present invention contemplates many methods to transfect the cells with the DNA-modifying reagent or reagents. Indeed, the present invention is not limited to any particular method. Methods for the introduction of DNA modifying reagents into a cell or cells are well known in the art and include, but are not limited to, microinjection, electroporation, passive adsorption, calcium phosphate-DNA co-precipitation, DEAE-dextran-mediated transfection, polybrene-mediated transfection, liposome fusion, lipofectin, protoplast fusion, retroviral infection, biolistics (i.e., particle bombardment) and the like.

One embodiment of the present invention provides a method wherein a plurality of cells, in which the cell cycle is synchronized, is exposed to at least 1 reagent capable of modifying the DNA of the cells, and testing the cells for modifications in their DNA. In another embodiment, the plurality of cells includes cells of more than one cell type. In a culture of multiple cell types, only the cell type of interest need be synchronized. In yet another embodiment, the cells are exposed to the DNA modifying reagent or reagents at a specific point in the cell cycle of the synchronized cells. In another embodiment, the DNA modifying reagents comprise TFOs. In yet another embodiment, the cell cycle synchronized cells are mammalian. In yet another embodiment, the cell cycle synchronized cells are zygotes.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques used involve recombinant nucleic acid methods, polynucleotide synthesis, cell and microbial culture, transformation (e.g., electroporation, lipofection) microscopy and flow cytometry. Generally enzymatic reactions and purification steps are performed according to the manufacturer's specifications. The techniques and procedures are generally performed according to conventional methods in the art and various general references (see, e.g., Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.).

It is contemplated that oligonucleotides including triplex forming oligonucleotides be synthesized using any suitable method (e.g., on an Applied BioSystems oligonucleotide synthesizer) (see Sinha et al., Nucleic Acids Res. 12:4539, 1984), according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [g-$^{32}$P]ATP and T4 polynucleotide kinase. Salts and unincorporated nucleotides are removed by chromatography on Sephadex G columns.

Determination of the Target Sequence

Target sequences may be determined for any gene sequence of interest including those found within databases such as GenBank (http://www.ncbi.nlm.nih.gov/PubMed/index.html). However, the target sequence may be contained in any gene for which the sequence is at least partially known. Target sequences within the gene sequence may be determined by the results desired. As mentioned above, the replacement, deletion or addition of specific sequences requires the determination of that particular sequence and the appropriate homologous sequence. For the embodiment in which inhibition of expression of a particular gene is involved, the selection of a sequence to which homology is needed need not be made with extreme precision. When using triple helix forming oligonucleotides, or other triple helix forming reagents such as PNAs, triple helix formation is enhanced when the target region is a polypurine or homopurine region.

Illustrative genomic sequences which may be modified using the invention's methods include, but are not limited to, sequences which encode enzymes; lymphokines (e.g., interleukins, interferons, TNF, etc.); growth factors (e.g., erythropoietin, G-CSF, M-CSF, GM-CSF, etc.); neurotransmitters or their precursors or enzymes responsible for synthesizing them; trophic factors (e.g., BDNF, CNTF, NGF, IGF, GMF, aFGF, bFGF, NT3, NT5, HARP/pleiotrophin, etc.); apolipoproteins (e.g., ApoAI, ApoAIV, ApoE etc.); lipoprotein lipase (LPL); the tumor-suppressing genes (e.g., p53, Rb, RapLA, DCC k-rev, etc.); factors involved in blood coagulation (e.g., Factor VII, Factor VIII, Factor IX, etc.); suicide genes (thymidine kinase or cytosine deaminase); blood products; hormones; etc.

In one embodiment, the genomic sequences encode enzymes and proteins which are involved in DNA repair. DNA repair enzymes and proteins are exemplified by, but not limited to, those which are involved in the nucleotide excision repair (NER) pathway, base excision repair (BER) pathway, double strand break repair (DSBR) pathway, error prone polymerases, and enzymes which are involved in direct repair of DNA modifications.

The nucleotide excision repair pathway is well characterized, and it recognizes and removes a wide variety of damaged bases. These might be the result of exposure of DNA to ultraviolet light, certain components of tobacco smoke, activated industrial chemicals (benzene, dyes, etc). The nucleotide excision repair machinery cuts out a 28-30 base piece of single strand DNA containing the adducted base. Then the resultant gap is filled in by a DNA polymerase and ligase. Nucleotide excision repair occurs most efficiently on transcribed sequences (transcription coupled repair), as well as on sequences that are non transcribed (global repair). The same kind of DNA adduct could be introduced into the nucleotide excision repair pathway by either transcription coupled repair or by global repair depending on the transcriptional status of the DNA in which it occurs. The enzymes of nucleotide excision repair also play a role in the repair of cross-links, such as those caused by psoralen. Exemplary enzymes and proteins of the nucleotide excision repair pathway include, but are not limited to, XPA, a protein involved in damage recognition; XPB, protein involved in unwinding of DNA in region of adduct; XPC, a protein involved in damage recognition-global repair; XPD, an enzyme involved in unwinding DNA in the region of the adduct; XPF, an enzyme involved in cutting DNA on the 5' side of the adduct; XPG, an enzyme involved in cutting DNA on the 3' side of adduct; ERCC1, a cofactor of the XPF enzyme; Cockayne's A, B which are proteins that function in transcription coupled repair. In particular, XPF and ERCC1 are involved in repair of adducts caused by crosslinking agents such as psoralen or mitomycin C. These two functions are important for crosslink repair. On the other hand, XPA, CSA, B, and XPC are involved in recognition, while the XPD, XPF, XPB, and XPD enzymes are involved in excision.

The base excision repair pathway repairs relatively small chemical changes, in contrast to the bulky lesions that are the responsibility of the nucleotide excision repair system. For example, the base excision repair pathway repairs oxidized bases which may be generated by radical oxygen species, ionizing radiation (e.g., X rays), and naphthalene diimide. In this pathway a single damaged base is removed by a glycosylase that cleaves the base-sugar bond. This is followed by cleavage of the sugar phosphate linkage by a lyase, then addition of one or a few bases at the nick by DNA polymerase beta, followed by cleavage of the damaged strand by Fen 1 nuclease, and ligation of the newly synthesized DNA. Exemplary enzymes of the base excision repair pathway include, but are not limited to, glycosylases which cut the base sugar linkage of damaged bases; lyase which cleaves the sugar phosphate linkage; DNA pol beta which extends nicked DNA one or a few bases; flap endonuclease (Fen1); and ligase which seals the nick. In a preferred embodiment the base excision repair enzyme is a glycosylase.

The double strand break repair pathway repairs double strand breaks which are caused by radical species, radiation, or radiation mimetics such as bleomycin or masked quinones. The radical species attack the phosphate backbone rather than the bases. Breaks are repaired by at least two subpathways. One involves the loss of small amounts of sequence at the site of a break and results in a deletion mutation. The second pathway requires an intact copy of the damaged sequence. This second copy is engaged in a recombinational process that eventually restores the broken sequence to its original state, and no mutation is generated. Exemplary enzymes and proteins of the double strand break repair pathway include, but are not limited to, Ku 70,86 which are end binding proteins that stabilize broken ends and recruit other proteins; DNA Pk which is a kinase that is recruited by the Ku complex and in turn activates other proteins; Mre11 complex which is a multiprotein complex involved in the repair of broken DNA; XRCC 2,3 which are proteins involved in homologous recombinational repair of breaks; Ligase IV which is a ligase involved in repair of breaks; and XRCC1 which is a cofactor of Ligase IV.

The error prone polymerases (iota, eta, zeta, etc) are DNA polymerases that have a relaxed fidelity and appear to be involved in polymerizing past sites of unrepaired DNA damage.

Enzymes which are involved in direct repair of DNA modifications include, but are not limited to, methyltransferases such as $O^6$-methylguanine-DNA methyltransferases which remove methyl groups from the $O^6$ position of guanine, $O^4$ position of thymine, and oxygens in the phospodiester backbone. Also included are photolyases such as DNA photolyase which removes cyclobutane pyrimidine dimers caused by UV irradiation.

In another preferred embodiment, the genomic sequences are those for which a mutant has been associated with a human disease. Such genomic sequences are exemplified, but not limited to, the adenosine deaminase (ADA) gene (GenBank Accession No. M13792) associated with adenosine deaminase deficiency with severe combined immune deficiency; alpha-1-antitrypsin gene (GenBank Accession No. M11465) associated with alpha1-antitrypsin deficiency; beta chain of hemoglobin gene (GenBank Accession No. NM_000518) associated with beta thalassemia and Sickle cell disease; receptor for low density lipoprotein gene (GenBank Accession No. D16494) associated with familial hypercholesterolemia; lysosomal glucocerebrosidase gene (GenBank Accession No. K02920) associated with Gaucher disease; hypoxanthine-guanine phosphoribosyltransferase (HPRT) gene (GenBank Accession No. M26434, J00205, M27558, M27559, M27560, M27561, M29753, M29754, M29755, M29756, M29757) associated with Lesch-Nyhan syndrome; lysosomal arylsulfatase A (ARSA) gene (GenBank Accession No. NM_000487) associated with metachromatic leukodystrophy; ornithine transcarbamylase (OTC) gene (GenBank Accession No. NM_000531) associated with ornithine transcarbamylase deficiency; phenylalanine hydroxylase (PAH) gene (GenBank Accession No. NM_000277) associated with phenylketonuria; purine nucleoside phosphorylase (NP) gene (GenBank Accession No. NM_000270) associated with purine nucleoside phosphorylase deficiency; the dystrophin gene (GenBank Accession Nos. M18533, M17154, and M18026) associated with muscular dystrophy; the utrophin (also called the dystrophin related protein) gene (GenBank Accession No. NM_007124) whose protein product has been reported to be capable of functionally substituting for the dystrophin gene; and the human cystic fibrosis transmembrane conductance regulator (CFTR) gene (GenBank Accession No.M28668) associated with cystic fibrosis.

Any type of cell which undergoes proliferation is expressly included within the scope of this invention. Such cells are exemplified by embryonic cells (e.g., oocytes, sperm cells, embryonic stem cells, 2-cell embryos, protocorm-like body cells, callus cells, etc.), adult cells (e.g., brain cells, fruit cells etc.), undifferentiated cells (e.g., fetal cells, tumor cells, etc.), differentiated cells (e.g., skin cells, liver cells, lung cells, breast cells, reproductive tract cells, neural cells, muscel cells, blood cells, T cells, B cells, etc.), dividing cells, senescing cells, cultured cells, and the like. Furthermore, the target cells may be primary cells or cultured cells. A "primary cell" is a cell which is directly obtained from a tissue or organ of an animal in the absence of culture. Preferably, though not necessarily, a primary cell is capable of undergoing ten or fewer passages in in vitro culture before senescence and/or cessation of proliferation. In contrast, a "cultured cell" is a cell which has been maintained and/or propagated in vitro. Cultured cells include "cell lines", i.e., cells which are capable of a greater number of passages in vitro before cessation of proliferation and/or senescence as compared to primary cells from the same source. A cell line includes, but does not require, that the cells be capable of an infinite number of passages in culture.

In one preferred embodiment, the cells are human and are exemplified, but not limited to, U937 cells (macrophage), ATCC# crl 1593.2; A-375 cells (melanoma/melanocyte), ATCC# crl-1619; KLE cells (uterine endometrium), ATCC# crl-1622; T98G cells (glioblastoma), ATCC# crl-1690; CCF-STTG1 cells (astrocytoma), ATCC# crl-1718; HUV-EC-C cells (vascular endothelium), ATCC# CRL-1730; UM-UC-3 cells (bladder), ATCC# crl-1749; CCD841-CoN cells (colon, ATCC# crl-1790; SNU-423 cells (hepatocellular carcinoma), ATCC# crl-2238; WI38 cells (lung, normal), ATCC# crl-75; Raji cells (lymphoblastoid), ATCC# ccl-86; BeWo cells (placenta, choriocarcinoma), ATCC# ccl-98; HT1080 cells (fibrosarcoma), ATCC# ccl-121; MIA PaCa2 cells (pancreas), ATCC# crl-1420; CCD-25SK cells (skin fibroblast), ATCC# crl-1474; ZR75-30 cells (mammary gland), ATCC# crl-1504; HOS cells (bone osteosarcoma), ATCC# crl-1543; 293-SF cells (kidney), ATCC# crl-1573; LL47 (MaDo) cells (normal lymphoblast), ATCC# ccl-135; and HeLa cells (cervical carcinoma), ATCC# ccl-2.

In another preferred embodiment, the cells are non-human and are exemplified, but not limited to, LM cells (mouse fibroblast), ATCC# ccl-1.2; NCTC 3526 cells (rhesus monkey kidney), ATCC# ccl-7.2; BHK-21 cells (golden hamster kidney), ATCC# ccl-10; MDBK cells (bovine kidney), ATCC# ccl-22; PK 15 cells (pig kidney), ATCC# ccl-33; MDCK cells (dog kidney), ATCC# ccl-34; PtK1 cells (kangaroo rat kidney), ATCC# ccl-35; Rk 13 cells (rabbit kidney), ATCC# ccl-37; Dede cells (Chinese hamster lung fibroblast), ATCC# ccl-39; Bu (IMR31) cells (bison lung fibroblast), ATCC# ccl-40; FHM cells (minnow epithelial), ATCC# ccl-42; LC-540 cells (rat Leydig cell tumor), ATCC# ccl-43; TH-1 cells (turtle heart epithelial), ATCC# ccl-50; E. Derm (NBL-6) cells (horse fibroblast), ATCC# ccl-57; MvLn cells (mink epithelial), ATCC# ccl-64; Ch1 Es cells (goat fibroblast), ATCC# ccl-73; P1 I Nt cells (raccoon fibroblast), ATCC# ccl-74; Sp I k cells (dolphin epithelial), ATCC# ccl-78; CRFK cells (cat epithelial), ATCC# ccl-94; Gekko Lung 1 cells (lizard-gekko epithelial), ATCC# ccl-111; Aedes Aegypti cells (mosquito epithelial), ATCC# ccl-125; ICR 134 cells (frog epithelial), ATCC# ccl-128; Duck embryo cells (duck fibroblast), ATCC# ccl-141; and DBS Fcl-1 cells (monkey lung fibroblast), ATCC# ccl-161.

In an alternative preferred embodiment, the cells are capable of generating an animal. Such cells are exemplified by, but not limited to, fertilized egg cells which may be implanted into the uterus of a pseudopregnant female and allowed to develop into an animal. These cells have successfully been used to produce transgenic mice, sheep, pigs, rabbits and cattle [Hammer et al., (1986) J. Animal Sci.:63: 269; Hammer et al., (1985) Nature 315:680-683]. Other cells include pre-implantation embryo cells. For example, blastomere cells [Jaenisch, (1976) Proc. Natl. Acad. Sci USA 73:1260-1264; [Jahner et al., .(1985) Proc. Natl. Acad. Sci. USA 82:6927-6931; Van der Putten et al., (1985) Proc. Natl. Acad Sci USA 82:6148-6152], and eight-cell embryo cells from which the zona pellucida has been removed [Van der Putten (1985), supra; Stewart et al., (1987) EMBO J. 6:383-388]. The pre-implantation embryos which are manipulated in accordance with the invention's methods may be transferred to foster mothers for continued development. Alternatively, cells may be at a later stage of embryonic development, such as blastocoele cells and midgestation embryo cells [Jahner et al., (1982) Nature 298:623-628]. Yet another cell type is an embryonic stem (ES) cell. ES cells are pluripotent cells which may be directly derived from, for example, the inner cell mass of blastocysts [Doetchman et al., (1988) Dev. Biol. 127:224-227], from inner cell masses [Tolcunaga et al., (1989) Jpn. J. Anim. Reprod. 35:173-178], from disaggregated morulae [Eistetter, (1989) Dev. Gro. Differ. 31:275-282] or from primordial germ cells [Matsui et al., (1992) Cell 70:841-847]. Transgenic mice may be generated from ES cells which have been treated in accordance with the invention's methods by injection of several ES cells into the blastocoel cavity of intact blastocysts [Bradley et al., (1984) Nature 309:225-256]. Alternatively, a clump of ES cells may be sandwiched between two eight-cell embryos [Bradley et al., (1987) in "Teratocarcinomas and Embryonic Stem Cells: A Practical Approach," Ed. Robertson E. J. (IRL, Oxford, U.K.), pp. 113-151; Nagy et al., (1990) Development 110:815-821]. Both methods result in germ line transmission at high frequency.

In an alternative preferred embodiment, the cells are DNA repair-deficient. Data provided herein demonstrate that the frequency of genomic DNA modification is increased in cells which are DNA repair-deficient. The terms "DNA repair-deficient" and "reduced level of at least one DNA repair polypeptide" refer to a quantity and/or activity of a DNA repair polypeptide which is less than, preferably at least 10% less than, more preferably at least 50% less than, yet more preferably at least 90% less than, the quantity and/or activity of the DNA repair polypeptide in a control cell (i.e., a corresponding cell type such a wild-type cell which contains the wild-type DNA repair polypeptide), and most preferably is at background level. When a background level or undetectable quantity and/or activity of a DNA repair polypeptide is measured, this may indicate that the DNA repair enzyme is absent. However, a "reduced level of at least one DNA repair polypeptide" need not, although it may, mean an absolute absence of the DNA repair polypeptide. The invention does not require, and is not limited to, methods in which the DNA repair polypeptide is 100% ablated. The quantity of a DNA repair polypeptide may be determined by, for example, enzyme linked immunosorbent assays. The activity of a DNA repair polypeptide may be determined using methods known in the art for each of the DNA repair enzymes and proteins.

The invention is not limited to the type of DNA repair polypeptide whose level is reduced in the cell. Rather, the invention expressly contemplates within its scope cells which contain reduced levels of any one or more DNA repair polypeptides which are exemplified by, but not limited to, XPA, XPB, XPC, XPD, XPF, XPG, ERCC1, Cockayne's A, B, DNA glycosylases, Fen1, DNA ligase, Ku 70,86 proteins, DNA Pk, Mre11 complex, XRCC 2,3, ligase IV, XRCC1, polymerase iota, polymerase eta, polymerase zeta, $O^6$-methylguanine-DNA methyltransferases, and DNA photolyase. Preferably, the DNA repair polypeptide whose level is reduced is one which is involved in the repair of the DNA modification which is introduced into the cell. For example, cells which are treated with a molecule which generates double strand breaks preferably contain a reduced level of one or more DNA repair polypeptides (e.g., Ku 70,86, Mre11 complex, XRCC 2,3, ligase IV, and XRCC1) which are involved in double strand break repair.

Examples of DNA-repair deficient cells which are contemplated to be within the scope of the invention include, but are not limited to, Chinese hamster cells described in Table 2, infra [i.e., UV24 cells, UV5 cells, UV61 cells, UV41 cells, IRS1 SF cells, XRV15B cells, EM9 cells, and V3 cells]; XP12Be cells (Human) which have a defective XPA gene that results in a defect in damage recognition; MB19tsA cells (mouse) which have a defective polbeta gene which encodes a polymerase in the base excision repair pathway; MO595 cells (human) which have a defective DNA Pk gene which encodes a kinase in the double strand break repair pathway; UV135 cells (hamster) which have a defective XPG gene that results in a defect in the nucleotide excision repair pathway; UV20 cells (hamster) which have a defective ERCC1 gene which encodes a nuclease cofactor in the nuclease excision repair pathway; GM00671 cells (human) which have a defective XPC gene which is involved in damage recognition in the nucleotide excision pathway; GM01588 cells (human) which have a defective ATM gene which encodes a damage sensor in end repair and double strand repair pathways; GM02359 cells (human) which have a defective XPV gene which encodes polymerase eta that functions in lesion bypass; GM00811 cells (human) which have a defective BIM gene which encodes a helicase; GM13705 cells (human) which have a defective BRCA1 gene which is involved in recombination repair; GM14170 cells (human) which have a defective BRCA2 gene which is involved in recombination repair; and AG03141 cells (human) which have a defective WRN gene which encodes a helicase.

The animals from which the target cells are derived are preferably mammalian. In a more preferred embodiment, the "mammal" is rodent, primate (including simian and human) ovine, bovine, ruminant, lagomorph, porcine, caprine, equine, canme, feline, ave, etc.

Synthesis of Triplex Forming Oligonucleotides

The synthesis of triplex forming oligonucleotides is well known in the art (see U.S. Pat. No. 5,962,426 to Glazer; U.S. Pat. No. 5,874,555 to Dervan et al. and US patent to Ts'o et al., issued Nov. 10, 1998, all of which are herein incorporated by reference). Also, triplex forming nucleotides may be purchased commercially (e.g., Glen Research, Sterling, Va.). Additionally, triplex forming oligonucleotides may be produced using a commercial nucleotide synthesizer.

Synthesis of Other DNA-Modifying Reagents

The synthesis of other reagents useful for modification of genomic DNA sequences are also well known in the art. For example, U.S. Pat. No. 5,986,053 to Ecker et al. and U.S. Pat. No. 5,539,082 to Nielsen et al., both of which are incorporated herein by reference, teach the synthesis of PNAs. Additionally, Dervan et al. U.S. Pat. No. 5,998,140, herein incorporated by reference) teaches the synthesis of oligomers of cyclic heterocycles. It is well know in the art how to induce genomic DNA mutations with PNAs (see, e.g., U.S. Pat. No. 5,641,625 issued to Ecker et al., herein incorporated by reference). In another example, Cook et al. (U.S. Pat. No. 6,025,482, herein incorporated by reference)

teaches the production of modified oligonucleotide analogs useful in forming triple helix structures with duplex DNA, and also teaches the modification of protein production or function in cells or organisms.

Additional methods of inducing modification and/or recombination may be used in conjunction with the present invention. For example, Wagner et al. (U.S. Pat. No. 4,873,191, and Wagner et al., *Proc Natl Acad Sci USA* 72:3619-3622, 1975, herein incorporated by reference) and Jansin et al. (U.S. Pat. No. 4,713,337, herein incorporated by reference) teach methods of recombination utilizing double-crossover events. Additionally, see Camerini-Otero (U.S. Pat. No. 5,460,941 and 5,570,473) Ferrin (U.S. Pat. No. 5,707,811) and Zoloshin (U.S. Pat. No. 5,731,811).

Introduction of DNA-Modifying Reagents into Recipient Cells

Any standard method known in the art may be utilized to introduce the DNA-modifying reagents and/or recombination-inducing reagents into the recipient cells. Such methods include, but are not limited to, microinjection, electroporation, passive adsorption, calcium phosphate-DNA co-precipitation, DEAE-dextran-mediated transfection, polybrene-mediated transfection, liposome fusion, lipofectin, protoplast fusion, retroviral infection, biolistics (i.e., particle bombardment) and the like. Particular cell types may be transfected with greater efficiency by one or more known methods. Processes of determining optimal conditions for transfection for a particular cell type are well known in the art, are practiced regularly and may be determined without undue experimentation.

Measuring DNA Modification and/or Recombination in the Recipient Cells

Methods for the measurement of DNA modification and/or recombination in the recipient cell or cells varies depending on the cell type used, the nature of the modification and/or homologous recombination in the cell and the physiological or morphological effect of the DNA-modifying and/or recombination event. The present invention is not limited to any particular method or methods used to determine the DNA modification and/or recombination in the recipient cell or cells. The contemplated methods are well known to those practiced in the art. For example, when the present invention is used for modifying the DNA or for the recombination of DNA in a zygote, the recombination event is expected to result in a change or changes in a physiological function or a morphological characteristic in the resulting organism. The expected change or changes can then be assayed or observed. Additionally, DNA samples obtained from the organism and changes in gene sequence can be determined by PCR (see, e.g., U.S. Pat. Nos. 4,683,195 and 4,683,202, to Mullis, hereby incorporated by reference).

In the case of cell lines or primary cell cultures, changes in physiology or morphology as the result of the modification and/or recombination event can be assayed and observed as desired. The assay used is determined by the nature of the physiological change mediated by the modification and/or recombination event. Additionally, DNA modification and/or genetic recombination can be assessed using PCR analysis, as detailed above.

Synchronization of Cell Cycle in Culture

Methods for the synchronization of the cell cycle of cultured cells are well known in the art. For example, one method separates rounded, mitotic cells from cultures of attached cells with mild agitation of the culture apparatus. Inhibitors of microtubule assembly such as trypostatin A (Usui et al., *Biochem J* 333:543-548, 1998), phomopsidin (Namikosh et al., *J Antibiot (Tokyo)* 50:890-892, 1997), colchicine and taxol (Sigma Chemical, St. Louis, Mo.) are also used to synchronize cell cycle. Other methods of cell cycle synchronization include thymidine block and DNA synthesis inhibition.

After exposure of the cells to any reagent suitable for cell cycle synchronization, the cells are monitored (as discussed below) to determine when the cells are at about the same point in the cell cycle. The cells in the culture progress to the stage in the cell cycle where the cell cycle block takes effect. Once a portion of the cells reach the cell cycle stage where the cell cycle block is effective, the reagent is washed away, usually by repeated gentle rinses (in the case of attachment dependent cells) or by repeated resuspension and centrifugation (in the case of suspension cells). There is no particular percentage of cells necessary to reach the cell cycle stage where the cell cycle blocking agent is effective. However, it is preferred that the portion of the cells at the cell cycle stage where the blocking agent is effective is at least 70% and preferably at least 90%. After washing, the cells reinitiate cell cycle progression at about the same rate. At this point the cells are considered to be synchronized. Synchrony is usually lost after several cell cycles as individual cells progress through the cell cycle at slightly differing rates.

Measuring Cell Cycle Synchronization

The present invention is not limited to any particular method to determine the extent of cell cycle synchronization or the phase of the cell cycle the population. However, many ways are known in the art to determine the cell cycle of a population of cells. The easiest, but least accurate, method is to look at the cells using light microscopy. The recognized phases of the cell cycle are easily discernable and the extent of synchronization can be determined by counting the percentage of cells at the inhibition point. When most of the cells have been cell cycle inhibited, the agent inducing the inhibition can be washed away thereby allowing the cells to begin cycling in synchrony.

More sophisticated methods for measuring cell cycle synchrony are available and may be more efficient, especially if large numbers of cell populations are to be examined. For example, flow cytometry can be used to determine the cell cycle stage of a sample of cells from a population. The sample is stained with a fluorescent dye that intercalates into the DNA (e.g., propidium iodide and acridine orange). The stained cell sample is then passed through the flow cytometer and a profile is generated that is indicative of the position of the cells in the cell cycle. Flow cytometry has the added advantage of allowing for the easy determination of the percentage of cells in the sample in any particular stage of the cell cycle.

Experimental

The following examples serve only to illustrate certain aspects of the present invention and in no way are meant to limit the present invention. Cited references are incorporated herein by reference.

EXAMPLE 1

Transfection Of Chinese Hamster Ovary Cells with Triplex Forming Oligonucleotides which Target the Examplary Hprt Gene In this example, the establishment of cell cultures used in the following experiment is described. CHO-K1 Chinese Hamster ovary cells (ATCC # CCL-61) were grown in Hams F12 (Gibco/BRL, Bethesda, Md.) medium containing 10% dialyzed calf serum. Prior to an experiment, cells were cultured in HAT medium ($10^{-4}$ M hypoxanthine, $5 \times 10^{-6}$ M aminopterin, $10^{-5}$ M thymidine) for one week to remove preexisting Hprt-deficient cells. Cells were electroporated in medium with TFOs (prepared as described in Example 2) at 10 μM and after 90 min treated with 365 nm light for 3 min with a dose of 1.8 J/cm². TFO concentrations of 5-10 μM were found to be optimal, with cell toxicity apparent at higher concentrations. The cells were carried in Hams F12 with 10% dialyzed calf serum for 8-10 days with 2-3 passages and then placed in selective (HAT) medium depleted of hypoxanthine and containing 20 μM 6TG. Cell aliquots were plated in selective (HAT) medium without 6TG (6-thioguanine nucleotide) to determine plating efficiency. After 10 days, resistant colonies were counted and picked for expansion and DNA isolation.

EXAMPLE 2

Preparation of Triplex Forming Oligonucleotides

In this example, the preparation of the TFOs used in Example 1 and other experiments is discussed. Psoralen was finked to the 5' end of TFOs by a C-6 linker (Glen Research, Sterling, Va.), and each residue carried a 2'-O methyl sugar modification which enhances triplex stability (see e.g., Escude et al., *Nucleic Acids Res* 21:5547-5553, 1993). All cytosines were methylated at the 5' position which improves triplex stability at physiological pH (see e.g., Posvic, et al, *J Am Chem Soc* 111:3059-3061, 1989 and Lee et al., *Nucleic Acids Res* 12:6603-6614, 1984). In extensive experiments with a minichromosome model, it was determined that the cytosine methylation was absolutely essential for in vivo targeting. Three residues at the 3' end of each TFO were thioated to provide nuclease resistance (see e.g., Gilar et al., *Nucleic Acids Res* 25:3615-3620, 1997; Agrawal et al., *Proc Natl Acad Sci USA* 94:2620-2625, 1997). In TFOs designated as 3-5 (see FIG. 1), the intercalator substitutions replaced a nucleotide and were incorporated so as to preserve the normal 3-carbon interphosphate distance (see e.g., Kukreti et al., *Nucleic Acids Res* 25:4264-4270, 1995). The intercalators were either prepared (see e.g., Korshn et al., *Nucleosides and Nucleotides* 16:1461-1464, 1997) (TFOs 3, 5) or obtained (TFO 4, Glen Research, Sterling, Va.) as phosphoramidites. TFOs 3 and 5 contained a pyrene attached by an 11-atom linker at the 18th position. A similar structure is available as a phosphoramidite (Cruachem, Ltd., Glasgow, Scotland, UK). TFO 4 contains an acridine at the 18th position. Oligonucleotides were synthesized on a Perceptives Expedite synthesizer (League City, Tex.) and purified by reverse phase HPLC, as per the manufacturers directions.

EXAMPLE 3

Analysis of Genomic DNA

In this example, the DNA analysis used in the other experiments is described. Mutant clones were expanded and genomic DNA extracted. Multiplex PCR analysis was performed as described (Rossiter et al, *Genomics* 9:247-256, 1991). Exon-5 PCR products were prepared in a single exon reaction and were treated with exonuclease to eliminate primers (USB). Sequence analysis was performed by a thermal cycle sequencing protocol (Sequitherm DNA sequencer, Epicentre Technologies, Madison, Wis.).

EXAMPLE 4

Triplex Forming Oligonucleotides Specifically Modify the Exemplary Hprt Gene in Chinese Hamster Ovary Cells During the development of the present invention, it had been found by the inventors that TFOs linked to psoralen could introduce deletions and precisely placed point mutations into a chromatinized, replicating shuttle vector plasmid, carrying triplex and psoralen target sites embedded in a variant supF mutation marker gene. In an attempt to extend this targeting strategy to an endogenous chromosomal locus, an appropriate polypyrimdine:polypurine sequence in the Chinese Hamster hypoxanthine phosphoribosyl transferase gene (Hprt; Rossiter et al., *Genomics* 9:247-256, 1991) was identified that was positioned immediately adjacent to the smallest exon, E5 (FIG. 1). The sequence has a run of 23 prymidines interrupted by a single purine. At the proximal end of the exon, there is a 5' TA step which can be crosslinked by psoralen. While T→C and T→A mutations are silent, all mutations at the A residue (the complementation of the second T in a T-Pso-T crosslink) inactivate the AG splice acceptor sequence (Schneider, *Nucleic Acids Res* 25:4408-4415, 1997; Cariello et al., *J Mol Biol* 231:41-57, 1993).

T→A inversions in an otherwise perfect purine:pyrimidine run were found to destabilize a triplex containing a pyrimidine third strand. A guanine placed at the position on a T→A inversion (see FIG. 1) is the best choice of the natural bases in a pyrimidine motif TFO (Griffin et al., *Science* 245:967-971, 1989; Fosselia et al., *Nucleic Acids Res* 21:4511-4515, 1993). Oligonucleotides linked to the intercalators pyrene and acridine have been described (Korshn et al., *Nucleosides and Nucleotides* 16:1461-1464, 1997; Orson et al., *J Am Chem Soc* 115:7908-7909, 1993; Kukreti et al., *Nucleic Acids Res* 25:4264-4270, 1997). Accordingly, a series of psoralen-linked TFOs (FIG. 1) designed to target the perfect 17-mer or the 23-mer sequence, was prepared. The longer oligos contained either a G or an intercalator (FIG. 1) at the inversion site. Cells that were mock electroporated and UVA treated yielded 5-20 6-thioguanine (6TG)-resistant colonies per $10^6$ clonable cells, typical of spontaneous Hprt mutation frequencies (Table 1). Cells treated with TFOs 1 and 2 showed either marginal or no increase in 6TG resistant colonies over the controls. PCR analysis of all exons, including E5, from these clones showed no obvious differences in PCR products as compared to spontaneous mutants (FIG. 2A). In addition, 84 E5 PCR products from several experiments were sequenced. Only two of these products contained mutations, both of which were small deletions. These data suggest that neither TFO 1 nor 2 were effective targeting reagents.

TABLE 1

Hprt-deficient colonies recovered after TFO-Pso treatment

| TFO | UVA | 6TG-resistant colonies/ $10^6$ cells |
|---|---|---|
| — | + | 5-20 |
| 1 | − | 12 |
| 1 | + | 29 |
| 2 | − | 21 |
| 2 | + | 29 |
| 1u | + | 18 |
| 1P⁻ | + | 9 |

TABLE 1-continued

Hprt-deficient colonies recovered after TFO-Pso treatment

| TFO | UVA | 6TG-resistant colonies/ $10^6$ cells |
|---|---|---|
| 3 | − | 8 |
| 3 | + | 115 |
| 4 | − | 16 |
| 4 | + | 108 |
| 5 | − | 16 |
| 5 | + | 122 |
| 4P− | + | 12 |
| 5P− | + | 18 |
| AG | + | 21 |
| TC | + | 17 |
| Hu | + | 15 |

AG (5'-Pso-AGGAAGGGGGGGGTGGTGGGGGAGGGGGAG-3') (SEQ ID NO:14) and TC (5'-Psi-TTTCTTTTTTCTTCTTTTCTTTCTTTTTCT-3') (SEQ ID NO:15) are psoralen oligonucleotides in the purine and pyrimidine motif, respectively. They do not bind the exon-5 triplex site. 1u is an unmodified version of TFO 1 linked to psoralen. 1P−, 4P−, and 5P− are fully modified versions of TFOs 1, 4 and 5 without psoralen. Hu is a psoralen oligo, equivalent to TFO 5, with the pyrene intercalator at position 18, directed against the E5 human sequence.

The activity of TFOs 3-5 were then examined. 6TG-resistant colonies were recovered at a level of about 1 per $10^4$ clonable cells. It is important to note that some mutations may be silent. It is also important to note that detection assays have finite limits of detection and may not reveal all mutations. In this regard, the data presented in this example is merely illustrative and is not intended to limit the present invention to any particular frequency of modification and/or recombination. PCR analysis showed that the patterns of all the exons except for E5 were similar to the patterns observed with spontaneous mutants. However, there were clear differences in electrophoretic mobility of many of the ES bands (FIG. 2B). Sequence analysis showed that of the 240 clones with mutations in the target region, 184 (77%) had deletions of 4-50 bases (FIG. 4) which extended from within the triplex region into E5. There were four mutations with one and six with two nucleotide deletions which removed either the A or the TA of the crosslink site (FIG. 3). There were also 10 (4%) base substitution mutations (FIG. 3). These were either tandem double base changes at the psoralen crosslink site or single base changes at the second position of the crosslink. Finally, there were 36 complex mutations (15%) that had both deletions of Hprt sequence in the triplex region and E5 and insertions of (2-1,000 bases) on non-Hprt sequence.

In addition, experiments were conducted to determine whether other features of the TFOs, unrelated to triplex formation and psoralen placement, might be responsible for the E5 mutagenesis. No increase in mutation frequency was observed with the introduction of TFOs without psoralen (1P−, 4P−) or a psoralen TFO with no protection against nucleases (1u, Table 1), which would have been degraded rapidly with the release of free psoralen. Furthermore, there is no bias towards mutagenesis of Hprt E5 following treatment of cells with free psoralen plus UVA (Laquerbe et al., Mutant Res 346:173-179, 1995). Two TFOs directed against sites used in model studies, one in the purine motif, AG-Pso (Wang et al., Mol Cell Biol 15:1759-1768, 1995), and the other in the pyrimidine motif, TC-Pso (Table 1), which had no affinity for the ES site, also failed to yield an increase in mutation frequency. In addition, a Pso-TFO, equivalent to TFO-5, designed to target the corresponding sequence in human cells, which has one less base (5 verses 6 adjacent thymidines) was tested. This TFO had no activity against the CHO target, although it was effective against the human target (Hu-Pso, Table 1). These results reflect the well established requirement for precise matching of TFO and target sequence for stable triplex formation (Thuong et al., Angew Chem Int Ed Engl 32:666-690, 1993).

There are two other polypyrimidine:polypurine sites in the Hprt gene, located next to exons 6 and 8. Although these would not be expected to form stable triplexes with TFOs 1-5, each has an adjacent psoralen-reactive site. Exons 6 and 8 in the 6TG-resistant clones from expedients with TFO 3-5 that failed to show changes in ES were examined. No instance of the small deletions that were typical of the E5 mutations were observed.

In addition, experiments were designated to determine whether mutagenesis was enhanced at another commonly employed mutation marker gene, Aprt, encoding adenine phosphoribosyl transferase, which also contains sequences with the potential for triplex formation with pyrimidine motif TFOs. No increase in the frequency of Aprt mutants relative to control cultures was observed. Although these experiments certainly do not address all possibilities, it appears that TFOs 3-5 did not attack other polypyrimidine:polypurine targets in the same or another gene.

Without limiting the invention to any particular mechanism, in these experiments, deletions might arise from either slipped mispairing during replication (Kunkel, Bioessays 14:303-308, 1992) which, in the case of a crosslink, occur during repair synthesis of a gapped (but still psoralen-linked) template, from processing of a double-strand break by exposure of single strands at the break followed by annealing at microhomologies, or from ligation of free ends with no requirement for microhomology (Sargent et al., Mol Cell Biol 17:267-277, 1997; Thacker et al., Nucleic Acids Res 20:6183-6188, 1992; Phillips et al., Mol Cell Biol 14:5794-5803, 1994). While not limiting the invention to any particular mechanism, approximately 50% of the deletions may be explained by simple end joining. However, the simplest explanation by the inventors that accounts for both kinds of deletions, as well as the insertions, is that they result from double-strand breaks, provoked by cellular processing of the TFO-psoralen crosslinks. Some of the same deletions were recovered in independent experiments, suggesting that there were preferred pathways for deletion formation. Nevertheless, an understanding of the mechanism is not required for using the present invention.

It should be noted that no increase in mutation frequency in experiments in which there was no activation of the psoralen was observed. In earlier work with the shuttle vector model (Wang et al., Science 271:802-805, 1996), it was found that treatment with non-psoralenated TFOs could induce mutations in the triplex region. However, the frequency of these mutations was 10-15-fold lower than that observed when the psoralen TFOs (with UVA) were used. Consequently, if there was some mutagenesis of Hprt due to the TFO alone, it is unlikely that it would have been detected over the spontaneous background.

The intercalator-TFOs form more stable triplexes than the unmodified versions (ukreti et al., Nucleic Acids Res 25:4264-4270, 1997), and this is the most probable explanation for their activity in these experiments. It is likely that the frequency of gene knockout in the present experiments is substantially lower than the level of binding activity of the TFOs. Only those oligos bound at the time of photoactivation can contribute to the mutagenesis. Furthermore, the level of crosslinks is reduced by endogenous DNA repair activity. Nonetheless, the demonstration that appropriately modified TFOs have access to chromosomal loci removes a conceptual barrier to their use for gene targeting and supports their development as reagents for gene knockout and sequence manipulation. It is contemplated that substantial increases in efficiency of gene knockout will be achieved by additional modifications to the oligonucleotides which increase their stability and triplex affinity, and by suppression of the relevant enzymes whose function it is to faithfully repair the oligo-psoralen crosslinks.

EXAMPLE 5

Figure 5:
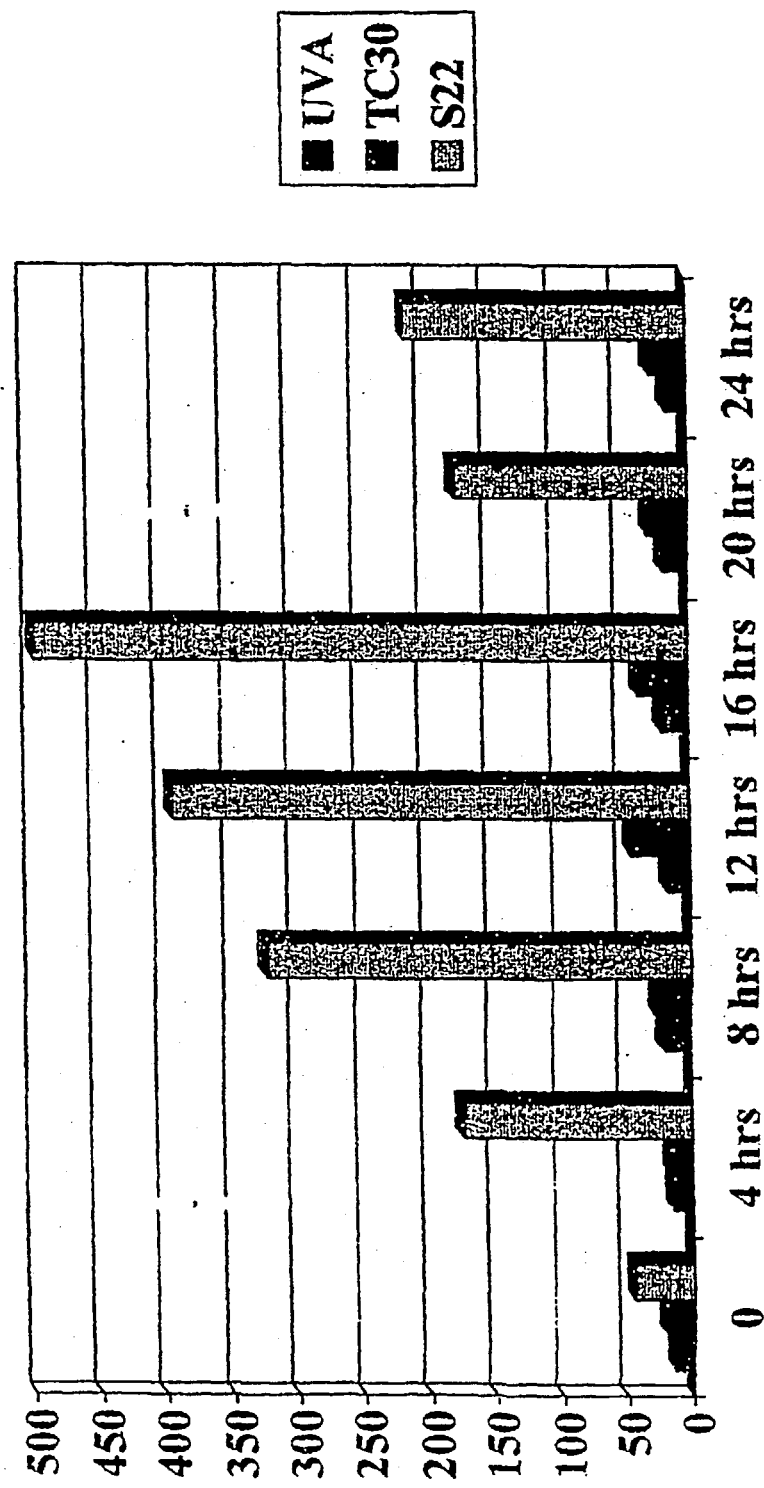
FIG. 5 shows the frequency of gene knockout (using a commonly employed mutation marker gene as a target) as a function of time from release from a treatment of cells which blocks them at the start of the cell cycle. TC30 is a non specific control oligo, S22 is the reagent in the absence of UVA, and UVA is the S22 reagent plus UVA activation.

Synchronizing the Cell Cycle of Chinese Hamster Ovary Cells Increases the Frequency of Modification of the Hprt Gene In this experiment, it is shown that cell cycle synchronization of the exemplary CHO-K1 cells at the S phase before transfection with the exemplary DNA modifying TFOs which contain psoralen results in a dramatic increase in targeted genomic modification. FIG. 5 shows the frequency of modification of the Hprt gene, which is commonly employed as a target for mutations, as a function of time from release from a treatment of cells which blocks them at the start of the cell cycle. As described above, the targeting TFO reagent carriers the mutagen psoralen which is activated by long wave ultraviolet light (UVA). The targeting reagent delivers the mutagen to the desired site, which upon activation causes chemical damage to the DNA which leads to mutations at the site. In FIG. 5, TC30 is a non specific control oligo, S22 is the reagent in the absence of UVA, and the UVA is the S22 reagent plus UVA activation. Only the combination of the correct reagent and the light activation gives a mutation signal. The mutation signal is designated TG resistant colonies, which refers to the specifics of the experimental selection protocol. The intensity of the signal can be influenced by cell cycle selection.

EXAMPLE 6

Synchronized Repair-Deficient Chinese Hamster Ovary Cells Show an Increased Frequency of Modification of the Hprt Gene This Example describes the experiments which were used to determine the effect of reducing the levels of DNA repair on the frequency of modification in the exemplary Hprt target gene in CHO cells. It was the inventor's consideration that genetic modification, including knockout mutagenesis, can be viewed as the endpoint of a series of molecular events. Thus DNA modifying reagents, such as TFOs, first find and bind their target sequence inside the nucleus of the cell, and then the DNA reactive component (e.g., psoralen) within the DNA modifying reagent reacts with the DNA to introduce a modification (e.g., crosslink). This modification would be recognized as a DNA damaging event by the cell and would trigger one or more of the several DNA repair pathways which process DNA damage. It was also the inventors' consideration that it is also possible that DNA damage might interfere with replication and/or transcription. Interference with either of these processes would also trigger cellular responses. Although some of the cellular functions might lead directly to mutagenesis (e.g., cutting out crosslinks might lead directly to a deletion mutation) the inventors considered that it is also possible that some repair action would lead to the simple, non-mutagenic removal of the DNA damage. It was the inventor's further consideration that if these non-mutagenic events were inhibited, then the frequency of modification, including knockout mutagenesis, may rise.

The inventor's hypothesis was tested and confirmed as follows. The knockout assay described in the above Examples was carried out using several chinese hamster ovary cell lines which were defective in different DNA repair functions. The frequencies of knockout mutation were recorded at the S phase. While higher TFO concentrations may be used, the frequencies were normalized to a TFO concentration of 1 μM in order to allow direct comparisons of TFO activity between different cell lines. In other words, the frequencies reported in Table 2 below do not necessarily reflect the highest frequency that may be obtained in an experiment since a TFO concentration greater than 1 μM may be used. Rather, the frequencies in Table 2 are minimal estimates.

TABLE 2

| | | Cells Tested | |
|---|---|---|---|
| Cell Line | Repair gene deficiency | Repair function** | KO Freq/TFO conc. (%)* |
| AA8 | gene | Wild type | 0.05 |
| UV24 | XPB gene | Helicase in NER | 0.12 |
| UV5 | XPD gene | Helicase in NER | 0.3 |
| UV61 | Cockayne's B | Component of Transcription coupled Repair | 0.8 |
| UV41 | XPF gene | Nuclease in NER | 1.0 |
| IRS1 SF | XRCC2 | Recombinational repair | 0.16 |
| XRV15B | Ku86 | End processing in break repair | 0.025 |
| EM9 | XRCC1 | Single strand break repair | 0.028 |
| V3 | DNA Pk | Double strand break | 0.015 |

*KO Freq/TFO conc. refers to the frequency of knockout mutations divided by the TFO concentration.
**NER (nucleotide excision repair) refers to a particular repair pathway.

Synchronization of DNA repair-deficient cells (for example, the CH0-UV61 cell line, which is defective in the gene for the Cockayne's B protein, a component of transcription coupled repair) at the S-phase prior to treatment with TFO-psoralen resulted in a significantly increased frequency of modification of the exemplary target Hprt gene when compared to un-synchronized CHO-UV61 cells (data not shown). These results demonstrate that the influence of the cell cycle position at the time of treatment with the DNA-modifying molecule is consistent regardles of whether the cells are DNA repair-proficient (e.g., CHO-A88 cells) or DNA repair-deficient (e.g., CHO-UV61 cells).

Importantly also, the results in Table 2 showed that the frequency of modification of the exemplary target Hprt gene in the DNA repair-deficient CHO-UV61 cells and CHO-UV41 cells was 16-fold and 20-fold greater, respectively, than the frequency of modification of the same target Hprt gene in the control DNA repair-proficient CHO-A88 cells. Indeed, the frequency of modification with the CHO-UV61 cell line was sufficiently high such that colonies could be screened directly, without selection, for mutations at the target site.

These data demonstrate that reducing the level of DNA repair in synchronized cells further increases the frequency of DNA modification by DNA modifying reagents. These data further demonstrate that the invention's methods are particularly advantageous in applications which relate to genomic sequences for which there are no selection strategies.

It should be clear from the above that the methods reported here allow for efficient modification and/or genetic recombination of target DNA sequences.

What is claimed is:

1. A method for modifying a target nucleotide sequence in a population of cells, comprising:
   a) producing a population of synchronized cells in vitro, wherein 75 to 100 percent of the cells in the population of cells are in S phase of the cell cycle, and wherein the cells comprise said target nucleotide sequence;
   b) contacting the population of synchronized cells with a triple helix forming oligonucleotide covalently linked to a DNA modifying agent under conditions such that a modification in the target nucleotide sequence is produced in the cells.

2. The method of claim 1, wherein the modification in the target nucleotide sequence is selected from the group consisting of deletion, insertion, substitution, strand break, and adduct formation.

3. The method of claim 1, wherein said triple helix forming oligonucleotide is from 5 to 100 nucleotides in length.

4. The method of claim 1, wherein said triple helix forming oligonucleotide is from 5 to 50 nucleotides in length.

5. The method of claim 1, wherein the cells are human cells.

6. The method of claim 1, wherein the cells are non-human cells.

7. The method of claim 1, wherein the cells are fertilized egg cells from an animal selected from the group consisting of mouse, sheep, pig, rabbit, and cattle.

8. The method of claim 1, wherein the cells are mouse cells selected from the group consisting of blastomere cells, eight-cell embryo cells blastocoele cells, midgestation embryo cells, and embryonic stem cells.

9. The method of claim 1, wherein the cells are DNA repair-deficient.

10. A method of mutating a specific target deoxyribonucleic acid (DNA) sequence in mammalian cells in a population of manimalian cells, comprising
    synchronizing the population of mammalian cells in vitro such that 75% to 100% of the mammalian cells are in S phase of the cell cycle; and
    introducing a DNA modifying molecule specific for the target DNA into the mammalian cells, wherein the DNA modifying molecule comprises a triple helix forming oligodexoynucleotide of 5 to 100 nucleotides in length that specifically binds the specific target DNA, wherein the triple helix forming oligodexoynucleotide is covalently linked to a cross-linking agent;
    thereby mutating the target DNA sequence in the mammalian cells in the population of mammalian cells.

11. The method of claim 10, wherein the mammalian cells are stem cells.

12. The method of claim 1, wherein the target nucleic acid sequence is within a nucleotide sequence that encodes an enzyme or a DNA binding protein.

13. The method of claim 1, wherein the target nucleic acid sequence is within a regulatory nucleic acid sequence.

14. The method of claim 1, wherein the DNA modifying agent is a DNA cross-linking agent.

15. The method of claim 14, wherein the cross-linking agent is psoralen.

16. The method of claim 10, wherein the cross-linking agent is psoralen.

* * * * *

SEQUENCE LISTING

```
<160> NUMBER OF SEQ ID NOS: 15

<210> SEQ ID NO 1
<211> LENGTH: 32
<212> TYPE: DNA
<213> ORGANISM: Cricetulus griseus

<400> SEQUENCE: 1
gattttcatt tctcttttt cttctagaat gt                                  32

<210> SEQ ID NO 2
<211> LENGTH: 32
<212> TYPE: DNA
<213> ORGANISM: Cricetulus griseus

<400> SEQUENCE: 2
acattctaga agaaaaaaga gaaatgaaaa tc                                 32

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
tttctctttt ttcttct                                                  17

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
ttttcgtttc tcttttttct tct                                           23

<210> SEQ ID NO 5
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: The residue between C at position 5 and T at
      position 6 is pyrene

<400> SEQUENCE: 5
ttttctttct cttttttctt ct                                            22

<210> SEQ ID NO 6
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (5)..(6)
<223> OTHER INFORMATION: The residue between C at position 5 and T at
      position 6 is acridine

<400> SEQUENCE: 6
ttttctttct cttttttctt ct                                            22

<210> SEQ ID NO 7
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: The residue between C at position 1 and T at
      position 2 is pyrene

<400> SEQUENCE: 7
ctttctcttt tttcttct                                                 18

<210> SEQ ID NO 8
<211> LENGTH: 56
<212> TYPE: DNA
<213> ORGANISM: Cricetulus griseus

<400> SEQUENCE: 8
ttcattttct gattttcatt tctctttttt tcttctgaat gtcttgattg ttgagg       56

<210> SEQ ID NO 9
<211> LENGTH: 55
<212> TYPE: DNA
<213> ORGANISM: Cricetulus griseus

<400> SEQUENCE: 9
ttcattttct gattttcatt tctctttttt tcttcgaatg tcttgattgt tgagg        55

<210> SEQ ID NO 10
<211> LENGTH: 57
<212> TYPE: DNA
<213> ORGANISM: Cricetulus griseus

<400> SEQUENCE: 10
ttcattttct gattttcatt tctctttttt tcttctggaa tgtcttgatt gttgagg      57

<210> SEQ ID NO 11
<211> LENGTH: 57
<212> TYPE: DNA
<213> ORGANISM: Cricetulus griseus

<400> SEQUENCE: 11
ttcattttct gattttcatt tctctttttt tcttcatgaa tgtcttgatt gttgagg      57

<210> SEQ ID NO 12
<211> LENGTH: 57
<212> TYPE: DNA
<213> ORGANISM: Cricetulus griseus

<400> SEQUENCE: 12
ttcattttct gattttcatt tctctttttt tcttcacgaa tgtcttgatt gttgagg      57

<210> SEQ ID NO 13
<211> LENGTH: 57
<212> TYPE: DNA
```

-continued

```
<213> ORGANISM: Cricetulus griseus

<400> SEQUENCE: 13
ttcattttct gattttcatt tctcttttt tcttctagaa tgtcttgatt gttgagg         57

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
aggaaggggg gggtggtggg ggaggggag                                       30

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
tttctttttt cttcttttct ttctttttct                                      30
```